United States Patent [19]
Bandman et al.

[11] Patent Number: 5,962,232
[45] Date of Patent: Oct. 5, 1999

[54] PROTEIN KINASE MOLECULES

[75] Inventors: Olga Bandman; Jennifer L. Hillman, both of Mountain View; Preeti Lal, Santa Clara; Ingrid E. Akerblom, Redwood City; Purvi Shah, Sunnyvale; Neil C. Corley, Mountain View; Karl J. Guegler, Menlo Park, all of Calif.

[73] Assignee: Incyte Pharmaceuticals, Inc., Palo Alto, Calif.

[21] Appl. No.: 09/016,000

[22] Filed: Jan. 30, 1998

[51] Int. Cl.⁶ .................. C12G 1/68; C12N 1/20; C12N 15/00; C07H 21/02
[52] U.S. Cl. .................. 435/6; 435/320.1; 435/325; 435/348; 435/252.3; 536/23.1; 536/23.5
[58] Field of Search .................. 435/6, 320.1, 325, 435/348, 252.3; 536/23.1, 23.5

[56] References Cited

PUBLICATIONS

Hillier et al. Genbank est database, accession No. H29221, Jul. 1995.

Hanks, S.K. and Hunter, T. "The Eukaryotic Protein Kinase Superfamily" *The Protein Kinase Facts Books*, Academic Press, San Diego, CA, I:7–20 (1995).

Bairoch, A. et al., "The PROSITE database, its status in 1995" *Nucleic Acids Res.* (1996) 24:189–196.

Isselbacher, K.J. et al., *Harrison's Principles of Internal Medicine* (1994) McGraw–Hill, New York, NY, pp. 416–431, 1887.

Haribabu, B., et al., "Human calcium–calmodulin dependent protein kinase I: cDNA cloning, domain structure and activation by phosphorylation at threonine–177 by calcium-–calmodulin dependent protein kinase I kinase", *The EMBO Journal*, (1995) 14:3679–3686.

Gao, G. et al., "Non–Catalytic β– and γ–Subunit Isoforms of the 5'–AMP–activated Protein Kinase" *J. Biol. Chem.* (1996) 271:8675–8681.

Egan, S.E. and Weinberg, R.A., "The pathway to signal achievement," *Nature* (1993) 365:781–783.

Li, B. et al., "prk, a Cytokine–inducible Human Protein Serine/Threonine Kinase Whose Expression Appears to be Down–regulated in Lung Carcinomas" *J. Biol. Chem.* (1996) 271:19402–19408.

Charbonneau, H. and Tonks, N.K., "1002 Protein Phosphatases?," *Annu.Rev.Cell Biol.*, (1992) 8:463–93.

*Primary Examiner*—Paula K. Hutzell
*Assistant Examiner*—Lin Sun-Hoffman
*Attorney, Agent, or Firm*—Incyte Pharmaceuticals, Inc.

[57] ABSTRACT

The invention provides human protein kinase molecules (HPKM) and polynucleotides which identify and encode HPKM. The invention also provides expression vectors, host cells, antibodies, agonists, and antagonists. The invention also provides methods for treating or preventing disorders associated with expression of HPKM.

9 Claims, No Drawings

PROTEIN KINASE MOLECULES

FIELD OF THE INVENTION

This invention relates to nucleic acid and amino acid sequences of a protein kinase molecules and to the use of these sequences in the diagnosis, treatment, and prevention of cancer and immune disorders.

BACKGROUND OF THE INVENTION

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domain is conserved and can be further subdivided into 11 subdomains. Each of the 11 subdomains contain specific residues and motifs or patterns of amino acids that are characteristic of that subdomain and are highly conserved. (Hardie, G. and Hanks, S. (1995) *The Protein Kinase Facts Books*, Vol I:7–20 Academic Press, San Diego, Calif.) In particular, two protein kinase signature sequences have been identified in the kinase domain, the first containing an active site lysine residue involved in ATP binding, and the second containing an aspartate residue important for catalytic activity. If a protein analyzed includes the two protein kinase signatures, the probability of that protein being a protein kinase is close to 100% (MOTIFS search program, Genetics Computer Group, Madison, Wis.; See e.g.,Bairoch, A., et al. (1996) Nucleic Acids Research 24(1), 189–196.)

The second messenger dependent protein kinases primarily mediate the effects of second messengers such as cyclic AMP (cAMP), cyclic GMP, inositol triphosphate, phosphatidylinositol, 3,4,5-triphosphate, cyclic ADPribose, arachidonic acid, diacylglycerol and calcium-calmodulin. The cyclic-AMP dependent protein kinases (PKA) are important members of the STK family. Cyclic-AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease. (Isselbacher, K. J. et al. (1994) *Harrison's Principles of Internal Medicine*, McGraw-Hill, New York, N.Y., pp. 416–431, 1887.)

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction, glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR. (Haribabu, B. et al. (1995) EMBO Journal 14:3679–86.) CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK). (Gao, G. et al. (1996) J. Biol Chem. 15:8675–81.) Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family, and they regulate intracellular signaling pathways. They mediate signal transduction from the cell surface to the nucleus via phosphorylation cascades. Several subgroups have been identified, and each manifests different substrate specificities and responds to distinct extracellular stimuli. (Egan, S. E. and Weinberg, R. A. (1993) Nature 365:781–783.) MAP kinase signaling pathways are present in mammalian cells as well as in yeast. The extracellular stimuli which activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). Altered MAP kinase expression is implicated in a variety of disease conditions including cancer, inflammation, immune disorders, and disorders affecting growth and development.

PRK (proliferation-related kinase) is a serum/cytokine inducible STK that is involved in regulation of the cell cycle and cell proliferation in human megakaroytic cells. (Li, B. et al. (1996) J. Biol. Chem. 271:19402–8.) PRK is related to the polo family of STKs implicated in cell division. PRK is downregulated in lung tumor tissue and may be a proto-oncogene whose deregulated expression in normal tissue leads to oncogenic transformation.

The cyclin-dependent protein kinases (CDKs) are another group of STKs that control the progression of cells through the cell cycle. Cyclins are small regulatory proteins that act by binding to and activating CDKs which then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity. (Carbonneau H and Tonks NK (1 992) Annu Rev Cell Biol 8:463–93.) Regulation of PTK activity may therefore be an important strategy in controlling some types of cancer.

The discovery of new protein kinase molecules and the polynucleotides encoding them satisfies a need in the art by providing new compositions which are useful in the diagnosis, treatment, and prevention of cancer and immune disorders.

SUMMARY OF THE INVENTION

The invention features substantially purified polypeptides, protein kinase molecules, referred to collectively as "HPKM" and individually as "HPKM-1", "HPKM-2", "HPKM-3", "HPKM-4", "HPKM-5", and "HPKM-6".

In one aspect, the invention provides a substantially purified polypeptide, HPKM, comprising an amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof.

The invention further provides a substantially purified variant of HPKM having at least 90% amino acid identity to the amino acid sequences of SEQ ID NO: 1, SEQ ID NO:2, SEQ ID NO:3, SEQ ID NO:4, SEQ ID NO:5, or SEQ ID NO:6, or fragments thereof. The invention also provides an isolated and purified polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof. The invention also includes an isolated and purified polynucleotide variant having at least 90% polynucleotide identity to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof.

Additionally, the invention provides a composition comprising a polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof. The invention further provides an isolated and purified polynucleotide which hybridizes under stringent conditions to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof, as well as an isolated and purified polynucleotide which is complementary to the polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof.

The invention also provides an isolated and purified polynucleotide comprising a polynucleotide sequence selected from the group consisting of SEQ ID NO:7, SEQ ID NO:8, SEQ ID NO:9, SEQ ID NO:10, SEQ ID NO:11, and SEQ ID NO:12, and fragments thereof. The invention further provides an isolated and purified polynucleotide variant having at least 90% polynucleotide identity to the polynucleotide comprising a polynucleotide sequence selected from the group consisting of SEQ ID NO:7, SEQ ID NO:8, SEQ ID NO:9, SEQ ID NO:10, SEQ ID NO:11, and SEQ ID NO:12, and fragments thereof, as well as an isolated and purified polynucleotide which is complementary to the polynucleotide comprising a polynucleotide sequence selected from the group consisting of SEQ ID NO:7, SEQ ID NO:8, SEQ ID NO:9, SEQ ID NO:10, SEQ ID NO:11, and SEQ ID NO:12 and fragments thereof.

The invention further provides an expression vector containing at least a fragment of the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, and SEQ ID NO:6, and fragments thereof. In another aspect, the expression vector is contained within a host cell.

The invention also provides a method for producing a polypeptide comprising the amino acid sequence of SEQ ID NO:1, SEQ ID NO:2, SEQ ID NO:3, SEQ ID NO:4, SEQ ID NO:5, SEQ ID NO:6, or fragments thereof, the method comprising the steps of: (a) culturing the host cell containing an expression vector containing at least a fragment of a polynucleotide encoding HPKM under conditions suitable for the expression of the polypeptide; and (b) recovering the polypeptide from the host cell culture.

The invention also provides a pharmaceutical composition comprising a substantially purified HPKM having the amino acid sequence of SEQ ID NO:1, SEQ ID NO:2, SEQ ID NO:3, SEQ ID NO:4, SEQ ID NO:5, SEQ ID NO:6, or fragments thereof in conjunction with a suitable pharmaceutical carrier.

The invention further includes a purified antibody which binds to a polypeptide comprising the amino acid sequence of SEQ ID NO:1, SEQ ID NO:2, SEQ ID NO:3, SEQ ID NO:4, SEQ ID NO:5, SEQ ID NO:6, or fragments thereof, as well as a purified agonist and a purified antagonist to the polypeptide.

The invention also provides a method for treating or preventing a cancer associated with increased expression or activity of HPKM, the method comprising administering to a subject in need of such treatment an effective amount of an antagonist of HPKM.

The invention also provides a method for treating or preventing an immune disorder associated with increased activity or expression of HPKM, the method comprising administering to a subject in need of such treatment an effective amount of an antagonist of HPKM.

The invention also provides a method for treating or preventing a cancer associated with decreased expression or activity of HPKM, the method comprising administering to a subject in need of such treatment an effective amount of a pharmaceutical composition comprising HPKM.

The invention also provides a method for treating or preventing an immune disorder associated with decreased activity or expression of HPKM, the method comprising administering to a subject in need of such treatment an effective amount of a pharmaceutical composition comprising HPKM.

The invention also provides a method for detecting a polynucleotide encoding HPKM in a biological sample containing nucleic acids, the method comprising the steps of: (a) hybridizing the complement of the polynucleotide sequence encoding the polypeptide comprising SEQ ID NO:1, SEQ ID NO:2, SEQ ID NO:3, SEQ ID NO:4, SEQ ID NO:5, SEQ ID NO:6, or fragments thereof to at least one of the nucleic acids of the biological sample, thereby forming a hybridization complex; and (b) detecting the hybridization complex, wherein the presence of the hybridization complex correlates with the presence of a polynucleotide encoding HPKM in the biological sample. In one aspect, the nucleic acids of the biological sample are amplified by the polymerase chain reaction prior to the hybridizing step.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HPKM," as used herein, refers to the amino acid sequences of substantially purified HPKM obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HPKM, increases or prolongs the duration of the effect of HPKM. Agonists may include proteins, nucleic acids, carbohydrates, or any other molecules which bind to and modulate the effect of HPKM.

An "allele" or an "allelic sequence," as these terms are used herein, is an alternative form of the gene encoding HPKM. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HPKM, as described herein, include those sequences with deletions, insertions, or substitutions of different nucleotides, resulting in a polynucleotide the same HPKM or a polypeptide with at least one functional characteristic of HPKM. Included within this definition are polymorphisms which may or may not be readily detectable using a particular oligonucleotide probe of the polynucleotide encoding HPKM, and improper or unexpected hybridization to alleles, with a locus other than the normal chromosomal locus for the polynucleotide sequence encoding HPKM. The encoded protein may also be "altered," and may contain deletions, insertions, or substitutions of amino acid residues which produce a silent change and result in a functionally equivalent HPKM. Deliberate amino acid substitutions may be made on the basis of similarity in polarity, charge, solubility, hydrophobicity, hydrophilicity, and/or the amphipathic nature of the residues, as long as the biological or immunological activity of HPKM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine;

asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HPKM which are preferably about 5 to about 15 amino acids in length and which retain some biological activity or immunological activity of HPKM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to HPKM, decreases the amount or the duration of the effect of the biological or immunological activity of HPKM. Antagonists may include proteins, nucleic acids, carbohydrates, antibodies, or any other molecules which decrease the effect of HPKM.

As used herein, the term "antibody" refers to intact molecules as well as to fragments thereof, such as Fa, $F(ab')_2$, and Fv fragments, which are capable of binding the epitopic determinant. Antibodies that bind HPKM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HPKM, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HPKM or fragments of HPKM may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HPKM, by northern analysis is indicative of the presence of nucleic acids encoding HPKM in a sample, and thereby correlates with expression of the transcript from the polynucleotide encoding HPKM.

A "deletion," as the term is used herein, refers to a change in the amino acid or nucleotide sequence that results in the absence of one or more amino acid residues or nucleotides.

The term "derivative," as used herein, refers to the chemical modification of HPKM, of a polynucleotide sequence encoding HPKM, or of a polynucleotide sequence complementary to a polynucleotide sequence encoding HPKM. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign program (DNASTAR, Inc., Madison Wis.). This program can create alignments between two or more sequences according to different methods, e.g., the clustal method. (Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, such as the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides or oligonucleotides on a substrate, such as paper, nylon or any other type of membrane, filter, chip, glass slide, or any other suitable solid support.

The term "modulate," as it appears herein, refers to a change in the activity of HPKM. For example, modulation may cause an increase or a decrease in protein activity, binding characteristics, or any other biological, functional, or immunological properties of HPKM.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HPKM, or fragments thereof, or HPKM itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and transiently transformed cells which express the inserted DNA or RNA for limited periods of time.

A "variant" of HPKM, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of new human protein kinase molecules (HPKM), the polynucleotides encoding HPKM and the use of these compositions for the diagnosis, treatment, or prevention of cancer and immune disorders. Table 1 shows the sequence identification numbers, Incyte Clone identification number, and CDNA library for each of the human protein kinase molecules disclosed herein.

TABLE 1

| PROTEIN | NUCLEOTIDE | CLONE ID | LIBRARY |
| --- | --- | --- | --- |
| SEQ ID NO:1 | SEQ ID NO:7 | 2940 | HMC1NOT01 |
| SEQ ID NO:2 | SEQ ID NO:8 | 307624 | HEARNOT01 |
| SEQ ID NO:3 | SEQ ID NO:9 | 339963 | NEUTFMT01 |
| SEQ ID NO:4 | SEQ ID NO:10 | 472480 | MMLR1DT01 |
| SEQ ID NO:5 | SEQ ID NO:11 | 1222984 | COLNTUT02 |
| SEQ ID NO:6 | SEQ ID NO:12 | 2061844 | OVARNOT03 |

Nucleic acids encoding the HPKM-1 of the present invention were first identified in Incyte Clone 2940 from the mast cell line cDNA library (HMC1NOT01) using a computer search for amino acid sequence alignments. A consensus sequence, SEQ ID NO:7, was derived from the following overlapping and/or extended nucleic acid sequences: Incyte Clones 002940 (HMC1NOT01), 161207 (ADENINB01), 1272707 (TESTTUT02), 1679482 (STOMFET01), 3279031 (STOMFET02), and 3933718 (PROSTUT09).

In one embodiment, the invention encompasses a polypeptide comprising the amino acid sequence of SEQ ID NO:1. HPKM-1 is 347 amino acids in length and has two potential N-glycosylation sites at N60 and N282, and potential phosphorylation sites for cAMP- and cGMP-dependent protein kinase at T235, for casein kinase II at T73, S111, T171, and S280, and for protein kinase C at T179, S230, 1284, S316, and S334. HPKM-1 contains two potential signature sequences for protein kinase catalytic domains. The first is the sequence L83 through K106, in which K106 is involved in ATP binding, and second is the sequence V199 through L211, in which D203 is important for catalytic activity of the enzyme. The fragment of SEQ ID NO:7 from about nucleotide 267 to about nucleotide 324 is useful as a hybridization probe. Northern analysis shows the expression of this sequence in fetal, hematopoietic, and immune system cDNA libraries. Approximately 41% of these libraries are associated with cancer and 41% with inflammation and the immune response.

Nucleic acids encoding the HPKM-2 of the present invention were first identified in Incyte Clone 307624 from the heart cDNA library (HEARNOT01) using a computer search for amino acid sequence alignments. A consensus sequence, SEQ ID NO:8, was derived from the following overlapping and/or extended nucleic acid sequences: Incyte Clones 307624 (HEARNOT01), 386290 (THYMNOT02), 529450 (BRAINOT03), and 3246426 (BRAINOT19).

In another embodiment, the invention encompasses a polypeptide comprising the amino acid sequence of SEQ ID NO:2. HPKM-2 is 688 amino acids in length and has a potential N-glycosylation site at residue N305, and potential phosphorylation sites for cAMP- and cGMP-dependent protein kinase at S676, for casein kinase II at S9, T41, S52, T121, T278, T328, T 338, T376, S429, T478, S497, T563, S588, S593, S640, and S676, and for protein kinase C at S5, S11, T338, S380, and S616. HPKM-2 contains two potential signature sequences for protein kinase catalytic domains. The first is the sequence L87 through K110, in which K110 is involved in ATP binding, and the sequence I210 through M222, in which D214 is important for catalytic activity of the enzyme. The fragment of SEQ ID NO:8 from about nucleotide 542 to about nucleotide 620 is useful as a hybridization probe. Northern analysis shows the expression of this sequence in cardiovascular, hematopoietic and immune, and reproductive cDNA libraries. Approximately 46% of these libraries are associated with cancer and 27% with inflammation and the immune response.

Nucleic acids encoding the HPKM-3 of the present invention were first identified in Incyte Clone 339963 from the peripheral blood granulocyte cDNA library (NEUTFMT01) using a computer search for amino acid sequence alignments. A consensus sequence, SEQ ID NO:9, was derived from the following overlapping and/or extended nucleic acid sequences: Incyte Clones 339963 (NEUTFMT01), 412791 (BRSTNOT01), 1757023 (PITUNOT03), 2543768 (UTRSNOT11), 2669808 (ESOGTUT02), 2695349 (UTRSNOT12), and 2938016 (THYMFET02).

In another embodiment, the invention encompasses a polypeptide comprising the amino acid sequence of SEQ ID NO:3. HPKM-3 is 451 amino acids in length and has a potential N-glycosylation site at residue N1 82, and potential phosphorylation sites for cAMP- and cGMP-dependent protein kinase at S33 and S112, for casein kinase II at S36, S61, T134, S215, T253, T298, and T435, for protein kinase C at S4,S22,S26,S105,S108, S112, S128, T283, S309, T374, and T431, and for tyrosine kinase at Y56 and Y67. HPKM-3 contains two potential signature sequences for protein kinase catalytic domains. The first is the sequence L135 through K159, in which K159 is involved in ATP binding, and the sequence I252 through F264, in which D256 is important for catalytic activity of the enzyme. The fragment of SEQ ID NO:9 from about nucleotide 377 to about nucleotide 434 is useful as a hybridization probe. Northern analysis shows the expression of this sequence in cardiovascular, male and female reproductive, nervous system, and hematopoietic and immune system cDNA libraries. Approximately 59% of these libraries are associated with cancer, and 30% with inflammation and the immune response.

Nucleic acids encoding the HPKM-4 of the present invention were first identified in Incyte Clone 472480 from the mononuclear cell cDNA library (MMLR1DT01) using a computer search for amino acid sequence alignments. A consensus sequence, SEQ ID NO:10, was derived from the following overlapping and/or extended nucleic acid sequences: Incyte Clones 472480 (MMLR1DT01), 2149576 (BRAINOT09), 2193812 (THYRTUT03), and 3123653 (LNODNOT05).

In another embodiment, the invention encompasses a polypeptide comprising the amino acid sequence of SEQ ID NO:4. HPKM-4 is 556 amino acids in length and has a potential signal peptide sequence between residues M1 and T31. A potential N-glycosylation sites is found at N520, and potential phosphorylation sites are found for casein kinase II at T31, T54, T104, S135,T148, S176, S191, S366, S398, S410, S431, and S549, for protein kinase C at T104, T226, T255 and, T322, and for tyrosine kinase at Y170. HPKM-4 contains two potential signature sequences for protein kinase catalytic domains. The first is the sequence L88 through K111, in which K 111 is involved in ATP binding, and the sequence I201 through L213, in which D205 is important for catalytic activity of the enzyme. The fragment of SEQ ID NO:10 from about nucleotide 338 to about nucleotide 451 is useful as a hybridization probe. Northern analysis shows the expression of this sequence in hematopoietic, immune, and nervous system cDNA libraries. Approximately 25% of these libraries are associated with cancer and 50% with inflammation and the immune response.

Nucleic acids encoding the HPKM-5 of the present invention were first identified in Incyte Clone 1222984 from the colon tumor cDNA library (COLNTUT02) using a computer search for amino acid sequence alignments. A consensus sequence, SEQ ID NO:11, was derived from the following overlapping and/or extended nucleic acid sequences: Incyte Clones 350627 (LVENNOT01), 451136 (TLYMNOT02), 871556 (LUNGAST01), 1222984 (COLNTUT02), and 2820464 (BRSTNOT14).

In another embodiment, the invention encompasses a polypeptide comprising the amino acid sequence of SEQ ID NO:5. HPKM-5 is 662 amino acids in length and has four potential N-glycosylation sites at residues N108, N175, N282, and N424. Potential phosphorylation sites are found for cAMP- and cGMP-dependent protein kinase at S107, for casein kinase II at S85, T110, S111, S120, T124, T252, T330, S456, S483, S500, T530, T582, and S639, for protein kinase C at T5, T267, S292, T400, S404, and S639, and for tyrosine kinase at Y343 and Y646. HPKM-2 has chemical and structural homology with human FAST kinase (GI 1006659). In particular, HPKM-2 and FAST kinase share 18% homology. HPKM-2 and FAST kinase share 7 cysteine residues, indicating potential similarities in secondary structure between the two proteins. The fragment of SEQ ID NO:11 from about nucleotide 849 to about nucleotide 900 is useful as a hybridization probe. Northern analysis shows the expression of this sequence in cardiovascular, gastrointestinal, and male and female reproductive cDNA libraries. Approximately 56% of these libraries are associated with cancer and 25% with inflammation and the immune response.

Nucleic acids encoding the HPKM-6 of the present invention were first identified in Incyte Clone 2061844 from the ovarian tissue cDNA library (OVARNOT03) using a computer search for amino acid sequence alignments. A consensus sequence, SEQ ID NO:12, was derived from the following overlapping and/or extended nucleic acid sequences: Incyte Clones 032341 (THP1NOB01), 1381117 and 1399865 (BRAITUT08), 1478515 and 1485886 (CORPNOT02), 1675310 (BLADNOT05), 2061844 (OVARNOT03), 2213079 (SINTFET03), 2516453 (LIVRTUT04), and 3684976 (HEAANOT01).

In another embodiment, the invention encompasses a polypeptide comprising the amino acid sequence of SEQ ID NO:6. HPKM-6 is 214 amino acids in length and has a potential N-glycosylation site at residue N132, and potential phosphorylation sites for cAMP- and cGMP-dependent protein kinase at T37, for casein kinase II at T61, S134, S146, and S165, and for protein kinase C at T17 and T105.

HPKM-6 contains two potential signature sequences for protein kinase catalytic domains. The first is the sequence L20 through K44, in which K44 is involved in ATP binding, and the sequence I133 through L145, in which D137 is important for catalytic activity of the enzyme. The fragment of SEQ ID NO:12 from about nucleotide 224 to about nucleotide 305 is useful as a hybridization probe. Northern analysis shows the expression of this sequence in male and female reproductive, nervous system, and hematopoietic immune cDNA libraries. Approximately 48% of these libraries are associated with cancer and 29% with inflammation and the immune response.

The invention also encompasses HPKM variants. A preferred HPKM variant is one which has at least about 80%, more preferably at least about 90%, and most preferably at least about 95% amino acid sequence identity to the HPKM amino acid sequence, and which contains at least one functional or structural characteristic of HPKM.

The invention also encompasses polynucleotides which encode HPKM. In a particular embodiment, the invention encompasses a polynucleotide sequence comprising the sequence of SEQ ID NO:7, SEQ ID NO:8, SEQ ID NO:9, SEQ ID NO:10, SEQ ID NO:11, or SEQ ID NO:12 which encodes an HPKM.

The invention also encompasses a variant of a polynucleotide sequence encoding HPKM. In particular, such a variant polynucleotide sequence will have at least about 80%, more preferably at least about 90%, and most preferably at least about 95% polynucleotide sequence identity to the polynucleotide sequence encoding HPKM. A particular aspect of the invention encompasses a variant of a polynucleotide sequence selected from the group consisting of SEQ ID NO:7, SEQ ID NO:8, SEQ ID NO:9, SEQ ID NO:10, SEQ ID NO:11, or SEQ ID NO:12 which has at least about 80%, more preferably at least about 90%, and most preferably at least about 95% polynucleotide sequence identity to a polynucleotide sequence selected from the group consisting of SEQ ID NO:7, SEQ ID NO:8, SEQ ID NO:9, SEQ ID NO:10, SEQ ID NO:11, or SEQ ID NO:12. Any one of the polynucleotide variants described above can encode an amino acid sequence which contains at least one functional or structural characteristic of HPKM.

It will be appreciated by those skilled in the art that as a result of the degeneracy of the genetic code, a multitude of polynucleotide sequences encoding HPKM, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HPKM, and all such variations are to be considered as being specifically disclosed.

Although nucleotide sequences which encode HPKM and its variants are preferably capable of hybridizing to the nucleotide sequence of the naturally occurring HPKM under appropriately selected conditions of stringency, it may be advantageous to produce nucleotide sequences encoding HPKM or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HPKM and its derivatives without altering the encoded amino acid sequences include the production of RNA transcripts having more desirable properties, such as a greater half-life, than transcripts produced from the naturally occurring sequence.

The invention also encompasses production of DNA sequences which encode HPKM and HPKM derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HPKM or any fragment thereof.

Also encompassed by the invention are polynucleotide sequences that are capable of hybridizing to the claimed polynucleotide sequences, and, in particular, to those shown in SEQ ID NO:1, SEQ ID NO:2, SEQ ID NO:3, SEQ ID NO:4, SEQ ID NO:5, SEQ ID NO:6, or fragments thereof under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Kienow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GiBco/BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HPKM may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPKM may be used in recombinant DNA molecules to direct expression of HPKM, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HPKM.

As will be understood by those of skill in the art, it may be advantageous to produce HPKM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HPKM-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HPKM may be ligated to a heterologous sequence to encode a fusion protein. For example, to screen peptide libraries for inhibitors of HPKM activity, it may be useful to encode a chimeric HPKM protein that can be recognized by a commercially available antibody. A fusion protein may also be engineered to contain a cleavage site located between the HPKM encoding sequence and the heterologous protein sequence, so that HPKM may be cleaved and purified away from the heterologous moiety.

In another embodiment, sequences encoding HPKM may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of HPKM, or a fragment thereof. For example, peptide synthesis can be performed using various solid-phase techniques. (See, e.g., Roberge, J. Y. et al. (1995) Science 269:202–204.) Automated synthesis may be achieved using the ABI 431 A Peptide Synthesizer (Perkin Elmer). Additionally, the amino acid sequence of HUPM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties*, WH Freeman and Co., New York, N.Y.)

In order to express a biologically active HPKM, the nucleotide sequences encoding HPKM or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HPKM and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9,13, and 16.)

A variety of expression vector/host systems may be utilized to contain and express sequences encoding HPKM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HPKM which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif.) or pSport1™ plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HPKM, vectors based on SV40 or EBV may be used with an appropriate selectable marker.

In bacterial systems, a number of expression vectors may be selected depending upon the use intended for HPKM. For example, when large quantities of HPKM are needed for the induction of antibodies, vectors which direct high level expression of fusion proteins that arc readily purified may be used. Such vectors include, but are not limited to, multifunctional *E. coli* cloning and expression vectors such as Bluescript® (Stratagene), in which the sequence encoding HPKM may be ligated into the vector in frame with sequences for the amino-terminal Met and the subsequent 7 residues of 13-galactosidase so that a hybrid protein is produced, and pSPORT vectors. (Gibco/BRL, Gaithersburg, Md.) pGEX vectors (Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HPKM may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HPKM. For example, in one such system, *Autographa californica* nuclear polyhedrosis virus (AcNPV) is used as a vector to express foreign genes in *Spodoptera frugiperda* cells or in Trichoplusia larvae. The sequences encoding HPKM may be cloned into a non-essential region of the virus, such as the polyhedrin gene, and placed under control of the polyhedrin promoter. Successful insertion of sequences encoding HPKM will render the polyhedrin gene inactive and produce recombinant virus lacking coat protein. The recombinant viruses may then be used to infect, for example, *S. frugiperda* cells or Trichoplusia larvae in which HPKM may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HPKM may be ligated into an adenovirus transcription/translation complex consisting of the late promoter and tripartite leader sequence. Insertion in a non-essential E1 or E3 region of the viral genome may be used to obtain a viable virus which is capable of expressing HPKM in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HPKM. Such signals include the ATG initiation codon and adjacent sequences. In cases where sequences encoding HPKM and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HPKM can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk$^-$ or apr$^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Recently, the use of visible markers, such as anthocyanins, green fluorescent proteins, β glucuronidase and its substrate GUS, luciferase and its substrate luciferin, has increased. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HPKM is inserted within a marker gene sequence, transformed cells containing sequences encoding HPKM can be identified by the absence of marker gene function. Alternatively, a marker gene can be placed in tandem with a sequence encoding HPKM under the control of a single promoter. Expression of the marker gene in response to induction or selection usually indicates expression of the tandem gene as well.

Alternatively, host cells which contain the nucleic acid sequence encoding HPKM and express HPKM may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HPKM can be detected by DNA-DNA or DNA-RNA hybridization or amplification using probes or fragments or fragments of polynucleotides encoding HPKM. Nucleic acid amplification based assays involve the use of oligonucleotides or oligomers based on the sequences encoding HPKM to detect transformants containing DNA or RNA encoding HPKM.

A variety of protocols for detecting and measuring the expression of HPKM, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HPKM is preferred, but a competitive binding assay may be employed. These and other assays are well described in the art. (See, e.g., Hampton, R. et al. (1990) Serological Methods a Laboratory Manual, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPKM include oligolabeling, nick translation, end-labeling, or PCR amplification using a labeled nucleotide. Alternatively, the sequences encoding HPKM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HPKM may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HPKM may be designed to contain signal sequences which direct secretion of HPKM through a prokaryotic or eukaryotic cell membrane. Other constructions may be used to join sequences encoding HPKM to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HPKM encoding sequence may be used to facilitate purification. One such expression vector provides for expression of a fusion protein containing HPKM and a nucleic acid encoding 6 histidine residues preceding a thioredoxin or an enterokinase cleavage site. The histidine residues facilitate purification on immobilized metal ion affinity chromatography. (IMAC) (See, e.g., Porath, J. et al. (1992) Prot. Exp. Purif. 3: 263–281.) The enterokinase cleavage site provides a means for purifying HPKM from the fusion protein. (See, e.g., Kroll, D. J. et al. (1993) DNA Cell Biol. 12:441–453.)

Fragments of HPKM may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the Applied Biosystems 431 A Peptide Synthesizer (Perkin Elmer). Various fragments of HPKM may be synthesized separately and then combined to produce the full length molecule.

THERAPEUTICS

Chemical and structural homology exists among the human protein kinase molecules of the invention. In addition, HPKM is expressed in cancer and in the immune response. Therefore, HPKM appears to play a role in cancer and immune disorders. Therefore, in cancer or immune disorders where HPKM is being expressed, it is desirable to decrease the expression of HPKM. In cancer or immune disorders where expression of HPKM is decreased, it is desirable to provide the protein or increase the expression of HPKM.

Therefore, in one embodiment, HPKM or a fragment or derivative thereof may be administered to a subject to treat or prevent a cancer associated with decreased expression or activity of HPKM. Such cancers can include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HPKM or a fragment or derivative thereof may be administered to a subject to treat or prevent a cancer including, but not limited to, those described above.

In a further embodiment, a pharmaceutical composition comprising a substantially purified HPKM in conjunction with a suitable pharmaceutical carrier may be administered to a subject to treat or prevent a cancer including, but not limited to, those provided above.

In still another embodiment, an agonist which modulates the activity of HPKM may be administered to a subject to treat or prevent a cancer including, but not limited to, those listed above.

In another embodiment, HPKM or a fragment or derivative thereof may be administered to a subject to treat or prevent an immune disorder associated with decreased expression or activity of HPKM. Such immune disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dernatitis, Crohn's disease, atopic dermatitis, dermatomyositis, diabetes mellitus, emphysema, crythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In another embodiment, a vector capable of expressing HPKM or a fragment or derivative thereof may be administered to a subject to treat or prevent an immune disorder including, but not limited to, those described above.

In a further embodiment, a pharmaceutical composition comprising a substantially purified HPKM in conjunction with a suitable pharmaceutical carrier may be administered to a subject to treat or prevent an immune disorder including, but not limited to, those provided above.

In still another embodiment, an agonist which modulates the activity of HPKM may be administered to a subject to treat or prevent an immune disorder including, but not limited to, those listed above.

In a further embodiment, an antagonist of HPKM may be administered to a subject to treat or prevent a cancer associated with increased expression or activity of HPKM. Such a cancer may include, but is not limited to, those discussed above. In one aspect, an antibody which specifically binds HPKM may be used directly as an antagonist or indirectly as a targeting or delivery mechanism for bringing a pharmaceutical agent to cells or tissue which express HPKM.

In an additional embodiment, a vector expressing the complement of the polynucleotide encoding HPKM may be administered to a subject to treat or prevent a cancer including, but not limited to, those described above.

In a further embodiment, an antagonist of HPKM may be administered to a subject to treat or prevent an immune disorder associated with increased expression or activity of HPKM. Such an immune disorder may include, but is not limited to, those discussed above. In one aspect, an antibody which specifically binds HPKM may be used directly as an antagonist or indirectly as a targeting or delivery mechanism for bringing a pharmaceutical agent to cells or tissue which express HPKM.

In an additional embodiment, a vector expressing the complement of the polynucleotide encoding HPKM may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HPKM may be produced using methods which are generally known in the art. In particular, purified HPKM may be used to produce antibodies or to screen libraries of pharmaceutical agents to identify those which specifically bind HPKM. Antibodies to HPKM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HPKM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HPKM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HPKM amino acids may be fused with those of another protein, such as KLH, and antibodies to the chimeric molecule may be produced.

Monoclonal antibodies to HPKM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HPKM-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HPKM may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPKM and its specific antibody. A two-site, monoclonal-based immunoassay utilizing monoclonal antibodies reactive to two non-interfering HPKM epitopes is preferred, but a competitive binding assay may also be employed. (Maddox, supra.)

In another embodiment of the invention, the polynucleotides encoding HPKM, or any fragment or complement thereof, may be used for therapeutic purposes. In one aspect, the complement of the polynucleotide encoding HPKM may be used in situations in which it would be desirable to block the transcription of the mRNA. In particular, cells may be transformed with sequences complementary to polynucleotides encoding HPKM. Thus, complementary molecules or fragments may be used to modulate HPKM activity, or to achieve regulation of gene function. Such technology is now well known in the art, and sense or antisense oligonucleotides or larger fragments can be designed from various locations along the coding or control regions of sequences encoding HPKM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HPKM. (See, e.g., Sambrook, supra; and Ausubel, supra.)

Genes encoding HPKM can be turned off by transforming a cell or tissue with expression vectors which express high levels of a polynucleotide, or fragment thereof, encoding HPKM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HPKM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HPKM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HPKM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HPKM, antibodies to HPKM, and mimetics, agonists, antagonists, or inhibitors of HPKM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HPKM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HPKM or fragments thereof, antibodies of HPKM, and agonists, antagonists or inhibitors of HPKM, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of therapeutic to toxic effects is the therapeutic index, and it can be expressed as the ED50/LD50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HPKM may be used for the diagnosis of disorders characterized by expression of HPKM, or in assays to monitor patients being treated with HPKM or agonists, antagonists, or inhibitors of HPKM. Antibodies useful for diagnostic purposes may be prepared in the same manner as described above for therapeutics. Diagnostic assays for HPKM include methods which utilize the antibody and a label to detect HPKM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HPKM, including ELISAs, RIAs, and FACS, are known in the art and provide a basis for diagnosing altered or abnormal levels of HPKM expression. Normal or standard values for HPKM expression are established by combining body fluids or cell extracts taken from normal mammalian subjects, preferably human, with antibody to HPKM under conditions suitable for complex formation The amount of standard complex formation may be quantitated by various methods, preferably by photometric means. Quantities of HPKM expressed in subject, control, and disease samples from biopsied tissues are compared with the standard values. Deviation between standard and subject values establishes the parameters for diagnosing disease.

In another embodiment of the invention, the polynucleotides encoding HPKM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HPKM may be correlated with disease. The diagnostic assay may be used to determine absence, presence, and excess expression of HPKM, and to monitor regulation of HPKM levels during therapeutic intervention.

In one aspect, hybridization with PCR probes which are capable of detecting polynucleotide sequences, including genomic sequences, encoding HPKM or closely related molecules may be used to identify nucleic acid sequences which encode HPKM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HPKM, alleles, or related sequences.

Probes may also be used for the detection of related sequences, and should preferably contain at least 50% identity to the nucleotides from any of the HPKM encoding sequences. The hybridization probes of the subject invention may be DNA or RNA and may be derived from the sequences of SEQ ID NO:7, SEQ ID NO:8, SEQ ID NO:9, SEQ ID NO:10, SEQ ID NO:11, or SEQ ID NO:12 or from genomic sequences including promoters, enhancers, and introns of the HPKM gene.

Means for producing specific hybridization probes for DNAs encoding HPKM include the cloning of polynucleotide sequences encoding HPKM or HPKM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HPKM may be used for the diagnosis of a disorder associated with expression of HPKM. Examples of such a disorder include, but are not limited to, cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis ,bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HPKM may be used in Southern or northern analysis, dot blot, or other membrane-based technologies; in PCR technologies; in dipstick, pin, and ELISA assays; and in microarrays utilizing fluids or tissues from patients to detect altered HPKM expression. Such qualitative or quantitative methods are well known in the art.

In a particular aspect, the nucleotide sequences encoding HPKM may be useful in assays that detect the presence of associated disorders, particularly those mentioned above. The nucleotide sequences encoding HPKM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HPKM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HPKM, a normal or standard profile for expression is established. This may be accomplished by combining body fluids or cell extracts taken from normal subjects, either animal or human, with a sequence, or a fragment thereof, encoding HPKM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HPKM may involve the use of PCR. These oligomers may be chemically synthesized, generated enzymatically, or produced in vitro. Oligomers will preferably contain a fragment of a polynucleotide encoding HPKM, or a fragment of a polynucleotide complementary to the polynucleotide encoding HPKM, and will be employed under optimized conditions for identification of a specific gene or condition. Oligomers may also be employed under less stringent conditions for detection or quantitation of closely related DNA or RNA sequences.

Methods which may also be used to quantitate the expression of HPKM include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1 995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1 997) U.S. Pat. No. 5,605,662.)

In another embodiment of the invention, nucleic acid sequences encoding HPKM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome CDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HPKM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HPKM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HPKM and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HPKM, or fragments thereof, and washed. Bound HPKM is then detected by methods well known in the art. Purified HPKM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPKM specifically compete with a test compound for binding HPKM. In this manner, antibodies can be used to detect the presence of any peptide which shares one or more antigenic determinants with HPKM.

In additional embodiments, the nucleotide sequences which encode HPKM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the OVARNOT03 cDNA library, from which Incyte Clone 2061844 was isolated, is described. Preparation and sequencing of cDNAs in libraries in the LIFESEQ™ database have varied over time, and the gradual changes involved use of kits, plasmids, and machinery available at the particular time the library was made and analyzed.

I. OVARNOT03 cDNA Library Construction

The OVARNOT03 cDNA library was constructed from microscopically normal ovary tissue obtained from a 43-year-old Caucasian female. Normal and tumorous tissues were excised when the patient underwent an unilateral salpingo-oophorectomy to remove an ovary which had been diagnosed with a malignant neoplasm. The patient history indicated a previous normal delivery and a vaginal hysterectomy. Noted were an unspecified viral hepatitis, cerebrovascular disease, atherosclerosis, and mitral valve disorder. Family history included malignant pancreatic cancer in the mother and malignant breast cancer in a grandparent.

The frozen tissue was homogenized and lysed in guanidinium isothiocyanate solution using a Brinkmann Homogenizer Polytron PT-3000 (Brinkmann Instruments, Westbury N.J.). The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted twice with acid phenol pH 4.0 following Stratagene's RNA isolation protocol, precipitated using 0.3 M sodium acetate and 2.5 volumes of ethanol, resuspended in DEPC-treated water, and DNase treated for 15 min at 37° C. The reaction was stopped with an equal volume of acid phenol, and the RNA was isolated with the Qiagen Oligotex kit (QIAGEN Inc, Chatsworth Calif.) and used to construct the cDNA library.

The RNA was handled according to the recommended protocols in the SuperScript Plasmid System for cDNA Synthesis and Plasmid Cloning (catalog #18248-013; Gibco/BRL), and cDNAs were ligated into pSport I. The plasmid pSport I was subsequently transformed into DH5a™ competent cells (Cat. #18258-012, Gibco/BRL).

II. Isolation and Sequencing of cDNA Clones

Plasmid or phagemid DNA was released from cells and purified using the Miniprep Kit (Cat. No. 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. No. 22711, Gibco/BRL) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R at 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA purification system (Cat. No. A7100, Promega) or QIAwell™-8 Plasmid, QIAwell PLUS DNA and QIAwell ULTRA DNA Purification Systems (Qiagen, Inc.).

The cDNAs were sequenced by the method of Sanger F. and A. R. Coulson (1975; J. Mol. Biol. 94:441f), using either a Catalyst 800 (ABI) or a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer), and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HPKM occurs. Abundance and percent abundance are also reported. Abundance directly reflects the number of times a particular transcript is represented in a cDNA library, and percent abundance is abundance divided by the total number of sequences examined in the cDNA library.

V. Extension of HPKM Encoding Polynucleotides

The sequence of one of the polynucleotides of the present invention was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat steps 4 through 6 for an additional 15 cycles
Step 8 94° C. for 15 sec
Step 9 65° C. for 1 min
Step 10 68° C. for 7:15 min
Step 11 Repeat steps 8 through 10 for an additional 12 cycles Step 12 72° C. for 8 min Step 13 4° C. (and holding)

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2×Carb. The following day, several colonies were randomly picked from each plate and cultured in 150 μl of liquid LB/2×Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec

Step 2 94° C. for 20 sec

Step 3 55° C. for 30 sec

Step 4 72° C. for 90 sec

Step 5 Repeat steps 2 through 4 for an additional 29 cycles

Step 6 72° C. for 180 sec

Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:7, SEQ ID NO:8, SEQ ID NO:9, SEQ ID NO: 10, SEQ ID NO:11, or SEQ ID NO:12 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:7, SEQ ID NO:8, SEQ ID NO:9, SEQ ID NO:10, SEQ ID NO:11, or SEQ ID NO: 12 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using or thermal, UV, mechanical, or chemical bonding procedures, or a vacuum system. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

In another alternative, full-length cDNAs or Expressed Sequence Tags (ESTs) comprise the elements of the microarray. Full-length cDNAs or ESTs corresponding to one of the nucleotide sequences of the present invention, or selected at random from a cDNA library relevent to the present invention, are arranged on an appropriate substrate, e.g., a glass slide. The cDNA is fixed to the slide using, e.g., U.V. cross-linking followed, by thermal and chemical and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

Probe sequences for microarrays may be selected by screening a large number of clones from a variety of cDNA libraries in order to find sequences with conserved protein motifs common to genes coding for signal sequence containing polypeptides. In one embodiment, sequences identified from cDNA libraries, are analyzed to identify those gene sequences with conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify functional or structural domains that cannot be detected using conserved motifs due to extreme sequence divergence. The method is based on weight matrices. Motifs identified by this method are then calibrated against the SWISS-PROT database in order to obtain a measure of the chance distribution of the matches.

In another embodiment, Hidden Markov models (HMMs) may be used to find shared motifs, specifically consensus sequences. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

VIII. Complementary Polynucleotides

Sequences complementary to the HPKM-encoding sequences, or any parts thereof, are used to detect, decrease, or inhibit expression of naturally occurring HPKM. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HPKM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HPKM-encoding transcript.

IX. Expression of HPKM

Expression of HPKM is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HPKM into bacterial growth media which can be used directly in the following assay for activity.

X. Demonstration of HPKM Activity

HPKM activity may be measured by phosphorylation of a protein substrate using gamma-labeled $^{32}$P-ATP and quantitation of the incorporated radioactivity using a gamma radioisotope counter. HPKM is incubated with the protein substrate, $^{32}$P-ATP, and a kinase buffer. The $^{32}$P incorporated into the substrate is then separated from free $^{32}$P-ATP by electrophoresis and the incorporated $^{32}$P is counted. The amount of $^{32}$P recovered is proportional to the activity of HPKM in the assay. A determination of the specific amino acid residues phosphorylated is made by phosphoamino acid analysis of the hydrolyzed protein.

XI. Production of HPKM Specific Antibodies

HPKM substantially purified using PAGE electrophoresis (see, e.g., Harrington, M. G. (1990) Methods Enzymol. 182:488–495), or other purification techniques, is used to immunize rabbits and to produce antibodies using standard protocols. The HPKM amino acid sequence is analyzed using DNASTAR software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems Peptide Synthesizer Model 431 A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HPKM Using Specific Antibodies

Naturally occurring or recombinant HPKM is substantially purified by immunoaffinity chromatography using antibodies specific for HPKM. An immunoaffinity column is constructed by covalently coupling anti-HPKM antibody to an activated chromatographic resin, such as CNBr-activated Sepharose (Pharmacia & Upjohn). After the coupling, the resin is blocked and washed according to the manufacturer's instructions.

Media containing HPKM are passed over the immunoaffinity column, and the column is washed under conditions that allow the preferential absorbance of HPKM (e.g., high ionic strength buffers in the presence of detergent). The column is eluted under conditions that disrupt antibody/HPKM binding (e.g., a buffer of pH 2 to pH 3, or a high concentration of a chaotrope, such as urea or thiocyanate ion), and HPKM is collected.

XIII. Identification of Molecules Which Interact with HPKM

HPKM, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HPKM, washed, and any wells with labeled HPKM complex are assayed. Data obtained using different concentrations of HPKM are used to calculate values for the number, affinity, and association of HPKM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polynucleotide sequence comprising an amino acid sequence of SEQ ID NO:3.

2. A composition comprising the polynucleotide sequence of claim 1.

3. An isolated and purified polynucleotide sequence which is completely complementary to the polynucleotide sequence of claim 1.

4. An isolated and purified polynucleotide sequence consisting of a polynucleotide sequence of SEQ ID NO:9.

5. An isolated and purified polynucleotide sequence which is completely complementary to the polynucleotide sequence of claim 4.

6. An expression vector containing the polynucleotide sequence of claim 1.

7. A host cell containing the expression vector of claim 6.

8. A method for detecting a polynucleotide encoding a polynucleotide sequence comprising the amino acid sequence of SEQ ID NO:3 in a biological sample containing nucleic acids, the method comprising the steps of:

(a) hybridizing the polynucleotide of claim 3 to the nucleic acids in the biological sample, thereby forming a hybridization complex; and (b) detecting the hybridization complex, wherein the presence of the hybridization complex correlates with the presence of a polynucleotide sequence encoding the polypeptide in the biological sample.

9. The method of claim 8 wherein the nucleic acids of the biological sample are amplified by the polymerase chain reaction prior to hybridization.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 347 amino acids
       (B) TYPE: amino acid
       (C) STRANDEDNESS: single
       (D) TOPOLOGY: linear (vii) IMMEDIATE SOURCE:
       (A) LIBRARY: HMC1NOT01
       (B) CLONE: 2940

(xi) SEQUENCE DESCRIPTION: SEQ ID NO:1:

Met Ala Gln Lys Glu Asn Ser Tyr Pro Trp Pro Tyr Gly Arg Gln Thr
 1               5                  10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
    130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Val Arg Ala Ile Met Glu Glu Leu Ala Asp Ala Leu Met
            180                 185                 190

Tyr Cys His Gly Lys Lys Val Ile His Arg Asp Ile Lys Pro Glu Asn
        195                 200                 205

Leu Leu Leu Gly Leu Lys Gly Glu Leu Lys Ile Ala Asp Phe Gly Trp
    210                 215                 220

Ser Val His Ala Pro Ser Leu Arg Arg Lys Thr Met Cys Gly Thr Leu
225                 230                 235                 240

Asp Tyr Leu Pro Pro Glu Met Ile Glu Gly Arg Met His Asn Glu Lys
                245                 250                 255

Val Asp Leu Trp Cys Ile Gly Val Leu Cys Tyr Glu Leu Leu Val Gly
            260                 265                 270

Asn Pro Pro Phe Glu Ser Ala Ser His Asn Glu Thr Tyr Arg Arg Ile
        275                 280                 285

Val Lys Val Asp Leu Lys Phe Pro Ala Ser Val Pro Thr Gly Ala Gln
    290                 295                 300

Asp Leu Ile Ser Lys Leu Leu Arg His Asn Pro Ser Glu Arg Leu Pro

```
305                 310                 315                 320
Leu Ala Gln Val Ser Ala His Pro Trp Val Arg Ala Asn Ser Arg Arg
                325                 330                 335
Val Leu Pro Pro Ser Ala Leu Gln Ser Val Ala
                340                 345
```

(2) INFORMATION FOR SEQ ID NO:2:

(i) SEQUENCE CHARACTERISTICS:
        (A) LENGTH: 688 amino acids
        (B) TYPE: amino acid
        (C) STRANDEDNESS: single
        (D) TOPOLOGY: linear (vii) IMMEDIATE SOURCE:
        (A) LIBRARY: HEARNOT01
        (B) CLONE: 307624

(xi) SEQUENCE DESCRIPTION: SEQ ID NO:2:

```
Met Ser Val Asn Ser Glu Lys Ser Ser Ser Glu Arg Pro Glu Pro
 1               5                  10                  15
Gln Gln Lys Ala Pro Leu Val Pro Pro Pro Pro Pro Pro Pro
                20                  25                  30
Pro Pro Pro Leu Pro Asp Pro Thr Pro Glu Pro Glu Glu Glu
                35                  40                  45
Ile Leu Gly Ser Asp Asp Glu Gln Glu Asp Pro Ala Asp Tyr Cys
 50                  55                  60
Lys Gly Gly Tyr His Pro Val Lys Ile Gly Asp Leu Phe Asn Gly Arg
 65                  70                  75                  80
Tyr His Val Ile Arg Lys Leu Gly Trp Gly His Phe Ser Thr Val Trp
                85                  90                  95
Leu Cys Trp Asp Met Gln Gly Lys Arg Phe Val Ala Met Lys Val Val
                100                 105                 110
Lys Ser Ala Gln His Tyr Thr Glu Thr Ala Leu Asp Glu Ile Lys Leu
                115                 120                 125
Leu Lys Cys Val Arg Glu Ser Asp Pro Ser Asp Pro Asn Lys Asp Met
                130                 135                 140
Val Val Gln Leu Ile Asp Asp Phe Lys Ile Ser Gly Met Asn Gly Ile
145                 150                 155                 160
His Val Cys Met Val Phe Glu Val Leu Gly His His Leu Leu Lys Trp
                165                 170                 175
Ile Ile Lys Ser Asn Tyr Gln Gly Leu Pro Val Arg Cys Val Lys Ser
                180                 185                 190
Ile Ile Arg Gln Val Leu Gln Gly Leu Asp Tyr Leu His Ser Lys Cys
                195                 200                 205
Lys Ile Ile His Thr Asp Ile Lys Pro Glu Asn Ile Leu Met Cys Val
                210                 215                 220
Asp Asp Ala Tyr Val Arg Arg Met Ala Ala Glu Ala Thr Glu Trp Gln
225                 230                 235                 240
Lys Ala Gly Ala Pro Pro Pro Ser Gly Ser Ala Val Ser Thr Ala Pro
                245                 250                 255
Gln Gln Lys Pro Ile Gly Lys Ile Ser Lys Asn Lys Lys Lys Lys Leu
                260                 265                 270
Lys Lys Lys Gln Lys Thr Gln Ala Glu Leu Leu Glu Lys Arg Leu Gln
                275                 280                 285
Glu Ile Glu Glu Leu Glu Arg Glu Ala Glu Arg Lys Ile Ile Glu Glu
                290                 295                 300
```

```
Asn Ile Thr Ser Ala Ala Pro Ser Asn Asp Gln Asp Gly Glu Tyr Cys
305                 310                 315                 320

Pro Glu Val Lys Leu Lys Thr Thr Gly Leu Glu Glu Ala Ala Glu Ala
                325                 330                 335

Glu Thr Ala Lys Asp Asn Gly Glu Ala Glu Asp Gln Glu Glu Lys Glu
                340                 345                 350

Asp Ala Glu Lys Glu Asn Ile Glu Lys Asp Glu Asp Val Asp Gln
            355                 360                 365

Glu Leu Ala Asn Ile Asp Pro Thr Trp Ile Glu Ser Pro Lys Thr Asn
370                 375                 380

Gly His Ile Glu Asn Gly Pro Phe Ser Leu Glu Gln Leu Asp Asp
385                 390                 395                 400

Glu Asp Asp Glu Glu Asp Cys Pro Asn Pro Glu Glu Tyr Asn Leu
                405                 410                 415

Asp Glu Pro Asn Ala Glu Ser Asp Tyr Thr Tyr Ser Ser Tyr Glu
                420                 425                 430

Gln Phe Asn Gly Glu Leu Pro Asn Gly Arg His Lys Ile Pro Glu Ser
                435                 440                 445

Gln Phe Pro Glu Phe Ser Thr Ser Leu Phe Ser Gly Ser Leu Glu Pro
                450                 455                 460

Val Ala Cys Gly Ser Val Leu Ser Glu Gly Ser Pro Leu Thr Glu Gln
465                 470                 475                 480

Glu Glu Ser Ser Pro Ser His Asp Arg Ser Arg Thr Val Ser Ala Ser
                485                 490                 495

Ser Thr Gly Asp Leu Pro Lys Ala Lys Thr Arg Ala Ala Asp Leu Leu
                500                 505                 510

Val Asn Pro Leu Asp Pro Arg Asn Ala Asp Lys Ile Arg Val Lys Ile
                515                 520                 525

Ala Asp Leu Gly Asn Ala Cys Trp Val His Lys His Phe Thr Glu Asp
530                 535                 540

Ile Gln Thr Arg Gln Tyr Arg Ser Ile Glu Val Leu Ile Gly Ala Gly
545                 550                 555                 560

Tyr Ser Thr Pro Ala Asp Ile Trp Ser Thr Ala Cys Met Ala Phe Glu
                565                 570                 575

Leu Ala Thr Gly Asp Tyr Leu Phe Glu Pro His Ser Gly Glu Asp Tyr
                580                 585                 590

Ser Arg Asp Glu Asp His Ile Ala His Ile Ile Glu Leu Leu Gly Ser
                595                 600                 605

Ile Pro Arg His Phe Ala Leu Ser Gly Lys Tyr Ser Arg Glu Phe Phe
610                 615                 620

Asn Arg Arg Gly Glu Leu Arg His Ile Thr Lys Leu Lys Pro Trp Ser
625                 630                 635                 640

Leu Phe Asp Val Leu Val Glu Lys Tyr Gly Trp Pro His Glu Asp Ala
                645                 650                 655

Ala Gln Phe Thr Asp Phe Leu Ile Pro Met Leu Glu Met Val Pro Glu
                660                 665                 670

Lys Arg Ala Ser Ala Gly Glu Cys Leu Arg His Pro Trp Leu Asn Ser
                675                 680                 685

(2) INFORMATION FOR SEQ ID NO:3:

(i) SEQUENCE CHARACTERISTICS:
        (A) LENGTH: 451 amino acids
        (B) TYPE: amino acid
        (C) STRANDEDNESS: single
        (D) TOPOLOGY: linear
```

(vii) IMMEDIATE SOURCE:
    (A) LIBRARY: NEUTFMT01
    (B) CLONE: 339963

(xi) SEQUENCE DESCRIPTION: SEQ ID NO:3:

```
Met Arg His Ser Lys Arg Thr His Cys Pro Asp Trp Asp Ser Arg Glu
 1               5                  10                  15

Ser Trp Gly His Glu Ser Tyr Arg Gly Ser His Lys Arg Lys Arg Arg
                20                  25                  30

Ser His Ser Ser Thr Gln Glu Asn Arg His Cys Lys Pro His His Gln
            35                  40                  45

Phe Lys Glu Ser Asp Cys His Tyr Leu Glu Ala Arg Ser Leu Asn Glu
        50                  55                  60

Arg Asp Tyr Arg Asp Arg Arg Tyr Val Asp Glu Tyr Arg Asn Asp Tyr
65                  70                  75                  80

Cys Glu Gly Tyr Val Pro Arg His Tyr His Arg Asp Ile Glu Ser Gly
                85                  90                  95

Tyr Arg Ile His Cys Ser Lys Ser Ser Val Arg Ser Arg Arg Ser Ser
                100                 105                 110

Pro Lys Arg Lys Arg Asn Arg His Cys Ser Ser His Gln Ser Arg Ser
            115                 120                 125

Met Lys Ser Val Asp Thr Leu Gly Glu Gly Ala Phe Gly Lys Val Val
        130                 135                 140

Glu Cys Ile Asp His Gly Met Asp Gly Met His Val Ala Val Lys Ile
145                 150                 155                 160

Val Lys Asn Val Gly Arg Tyr Arg Glu Ala Ala Arg Ser Glu Ile Gln
                165                 170                 175

Val Leu Glu His Leu Asn Ser Thr Asp Pro Asn Ser Val Phe Arg Cys
                180                 185                 190

Val Gln Met Leu Glu Trp Phe Asp His His Gly His Val Cys Ile Val
            195                 200                 205

Phe Glu Leu Leu Gly Leu Ser Thr Tyr Asp Phe Ile Lys Glu Asn Ser
210                 215                 220

Phe Leu Pro Phe Gln Ile Asp His Ile Arg Gln Met Ala Tyr Gln Ile
225                 230                 235                 240

Cys Gln Ser Ile Asn Phe Leu His His Asn Lys Leu Thr His Thr Asp
                245                 250                 255

Leu Lys Pro Glu Asn Ile Leu Phe Val Lys Ser Asp Tyr Val Val Lys
            260                 265                 270

Tyr Asn Ser Lys Met Lys Arg Asp Glu Arg Thr Leu Lys Asn Thr Asp
        275                 280                 285

Ile Lys Val Val Asp Phe Gly Ser Ala Thr Tyr Asp Asp Glu His His
290                 295                 300

Ser Thr Leu Val Ser Thr Arg His Tyr Arg Ala Pro Glu Val Ile Leu
305                 310                 315                 320

Ala Leu Gly Trp Ser Gln Pro Cys Asp Val Trp Ser Ile Gly Cys Ile
                325                 330                 335

Leu Ile Glu Tyr Tyr Leu Gly Phe Thr Val Phe Gln Thr His Asp Ser
                340                 345                 350

Lys Glu His Leu Ala Met Met Glu Arg Ile Leu Gly Pro Ile Pro Gln
            355                 360                 365

His Met Ile Gln Lys Thr Arg Lys Arg Lys Tyr Phe His His Asn Gln
        370                 375                 380

Leu Asp Trp Asp Glu His Ser Ser Ala Gly Arg Tyr Val Arg Arg Arg
```

```
       385                 390                 395                 400
Cys Lys Pro Leu Lys Glu Phe Met Leu Cys His Asp Glu Glu His Glu
                    405                 410                 415

Lys Leu Phe Asp Leu Val Arg Arg Met Leu Glu Tyr Asp Pro Thr Gln
                    420                 425                 430

Arg Ile Thr Leu Asp Glu Ala Leu Gln His Pro Phe Phe Asp Leu Leu
            435                 440                 445

Lys Lys Lys
    450

(2) INFORMATION FOR SEQ ID NO:4:

(i) SEQUENCE CHARACTERISTICS:
        (A) LENGTH: 556 amino acids
        (B) TYPE: amino acid
        (C) STRANDEDNESS: single
        (D) TOPOLOGY: linear (vii) IMMEDIATE SOURCE:
        (A) LIBRARY: MMLR1DT01
        (B) CLONE: 472480

(xi) SEQUENCE DESCRIPTION: SEQ ID NO:4:

Met Ala Arg Thr Thr Ser Gln Leu Tyr Asp Ala Val Pro Ile Gln Ser
  1               5                  10                  15

Ser Val Val Leu Cys Ser Cys Pro Ser Pro Met Val Arg Thr Gln
                 20                  25                  30

Thr Glu Ser Ser Thr Pro Pro Gly Ile Pro Gly Gly Ser Arg Gln Gly
             35                  40                  45

Pro Ala Met Asp Gly Thr Ala Ala Glu Pro Arg Pro Gly Ala Gly Ser
 50                  55                  60

Leu Gln His Ala Gln Pro Pro Gln Pro Arg Lys Lys Arg Pro Glu
 65                  70                  75                  80

Asp Phe Lys Phe Gly Lys Ile Leu Gly Glu Gly Ser Phe Ser Thr Val
                 85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
 130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270
```

-continued

```
Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
        290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
                355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
                435                 440                 445

His Gln Phe Val Glu Asn Asn Leu Ile Leu Lys Met Gly Pro Val Asp
        450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
                515                 520                 525

Ser Gly Asn Ala His Lys Trp Cys Arg Lys Ile Gln Glu Val Trp Arg
        530                 535                 540

Gln Arg Tyr Gln Ser His Pro Asp Ala Ala Val Gln
545                 550                 555
```

(2) INFORMATION FOR SEQ ID NO:5:

(i) SEQUENCE CHARACTERISTICS:
        (A) LENGTH: 662 amino acids
        (B) TYPE: amino acid
        (C) STRANDEDNESS: single
        (D) TOPOLOGY: linear (vii) IMMEDIATE SOURCE:
        (A) LIBRARY: COLNTUT02
        (B) CLONE: 1222984

(xi) SEQUENCE DESCRIPTION: SEQ ID NO:5:

```
Met Ala Leu Ile Thr Leu Arg Lys Asn Leu Tyr Arg Leu Ser Asp Phe
1               5                   10                  15

Gln Met His Arg Ala Leu Ala Ala Leu Lys Asn Lys Pro Leu Asn His
                20                  25                  30

Val His Lys Val Val Lys Glu Arg Leu Cys Pro Trp Leu Cys Ser Arg
                35                  40                  45

Gln Pro Glu Pro Phe Gly Val Arg Phe His His Ala His Cys Lys Lys
        50                  55                  60
```

-continued

```
Phe His Ser Lys Asn Gly Asn Asp Leu His Pro Leu Gly Gly Pro Val
 65                  70                  75                  80

Phe Ser Gln Val Ser Asp Cys Asp Arg Leu Glu Gln Asn Val Lys Asn
                 85                  90                  95

Glu Glu Ser Gln Met Phe Tyr Arg Arg Leu Ser Asn Leu Thr Ser Ser
            100                 105                 110

Glu Glu Val Leu Ser Phe Ile Ser Thr Met Glu Thr Leu Pro Asp Thr
            115                 120                 125

Met Ala Ala Gly Ala Leu Gln Arg Ile Cys Glu Val Glu Lys Lys Asp
130                 135                 140

Gly Asp Gln Gly Leu Pro Lys Gly Ile Leu Glu Asn Ser Ile Phe Gln
145                 150                 155                 160

Ala Leu Cys Phe Gln Phe Glu Lys Glu Pro Ser Gln Leu Ser Asn Thr
                165                 170                 175

Ser Leu Val Thr Ala Leu Gln Ala Leu Ile Leu Leu His Val Asp Pro
            180                 185                 190

Gln Ser Ser Leu Leu Leu Asn Leu Val Ala Glu Cys Gln Asn Arg Leu
            195                 200                 205

Arg Lys Gly Gly Met Glu Val Arg Asn Leu Cys Ile Leu Gly Glu Ser
210                 215                 220

Leu Ile Thr Leu His Ser Ser Gly Cys Val Thr Leu Glu Leu Ile Ile
225                 230                 235                 240

Asn Gln Leu Gln Gly Glu Lys Leu Glu Thr Phe Thr Pro Glu Asp Ile
                245                 250                 255

Val Ala Leu Tyr Arg Ile Leu Gln Ala Cys Thr Glu Lys Val Asp Glu
            260                 265                 270

His Gln Thr Phe Leu Asn Lys Ile Asn Asn Phe Ser Leu Ser Ile Val
            275                 280                 285

Ser Asn Leu Ser Pro Lys Leu Ile Ser Gln Met Leu Thr Ala Leu Val
290                 295                 300

Val Leu Asp Gln Ser Gln Ala Phe Pro Leu Ile Ile Lys Leu Gly Lys
305                 310                 315                 320

Tyr Val Val Arg His Val Pro His Phe Thr Asn Glu Glu Leu Arg Arg
                325                 330                 335

Val Leu Glu Ala Phe Ile Tyr Phe Gly His His Asp Thr Phe Phe Thr
            340                 345                 350

Lys Ala Leu Glu His Arg Val Ala Ala Val Cys Leu Thr Leu Asp Pro
            355                 360                 365

Glu Val Val Cys Arg Val Met Glu Tyr Cys Ser Arg Glu Leu Ile Leu
370                 375                 380

Ser Lys Pro Ile Leu Asn Ala Val Ala Glu Thr Phe Val Cys Gln Thr
385                 390                 395                 400

Glu Lys Phe Ser Pro Arg Gln Ile Ser Ala Leu Met Glu Pro Phe Gly
                405                 410                 415

Lys Leu Asn Tyr Leu Pro Pro Asn Ala Ser Ala Leu Phe Arg Lys Leu
            420                 425                 430

Glu Asn Val Leu Phe Thr His Phe Asn Tyr Phe Pro Pro Lys Ser Leu
            435                 440                 445

Leu Lys Leu Leu His Ser Cys Ser Leu Asn Glu Cys His Pro Val Asn
450                 455                 460

Phe Leu Ala Lys Ile Phe Lys Pro Leu Phe Leu Gln Arg Leu Gln Gly
465                 470                 475                 480

Lys Glu Ser His Leu Asp Thr Leu Ser Arg Ala Gln Leu Thr Gln Leu
```

```
                    485               490               495
Phe Leu Ala Ser Val Leu Glu Cys Pro Phe Tyr Lys Gly Pro Lys Leu
                500               505               510

Leu Pro Lys Tyr Gln Val Lys Ser Phe Leu Thr Pro Cys Cys Ser Leu
                515               520               525

Glu Thr Pro Val Asp Ser Gln Leu Tyr Arg Tyr Val Lys Ile Gly Leu
                530               535               540

Thr Asn Leu Leu Gly Ala Arg Leu Tyr Phe Ala Pro Lys Val Leu Thr
545                     550               555               560

Pro Tyr Cys Tyr Thr Ile Asp Val Glu Ile Lys Leu Asp Glu Glu Gly
                565               570               575

Phe Val Leu Pro Ser Thr Ala Asn Glu Asp Ile His Lys Arg Ile Ala
                580               585               590

Leu Cys Ile Asp Gly Pro Lys Arg Phe Cys Ser Asn Ser Lys His Leu
                595               600               605

Leu Gly Lys Glu Ala Ile Lys Gln Arg His Leu Gln Leu Leu Gly Tyr
                610               615               620

Gln Val Val Gln Ile Pro Tyr His Glu Ile Gly Met Leu Lys Ser Arg
625                     630               635               640

Arg Glu Leu Val Glu Tyr Leu Gln Arg Lys Leu Phe Ser Gln Asn Thr
                        645               650               655

Val His Trp Leu Gln Glu
                660

(2) INFORMATION FOR SEQ ID NO:6:

(i) SEQUENCE CHARACTERISTICS:
        (A) LENGTH: 214 amino acids
        (B) TYPE: amino acid
        (C) STRANDEDNESS: single
        (D) TOPOLOGY: linear (vii) IMMEDIATE SOURCE:
        (A) LIBRARY: OVARNOT03
        (B) CLONE: 2061844

(xi) SEQUENCE DESCRIPTION: SEQ ID NO:6:

Met Ala Gly Pro Gly Trp Gly Pro Pro Arg Leu Asp Gly Phe Ile Leu
1               5                   10                  15

Thr Glu Arg Leu Gly Ser Gly Thr Tyr Ala Thr Val Tyr Lys Ala Tyr
                20                  25                  30

Ala Lys Lys Asp Thr Arg Glu Val Ala Ile Lys Cys Val Ala Lys
                35                  40                  45

Lys Ser Leu Asn Lys Ala Ser Val Glu Asn Leu Leu Thr Glu Ile Glu
                50                  55                  60

Ile Leu Lys Gly Ile Arg His Pro His Ile Val Gln Leu Lys Asp Phe
65                  70                  75                  80

Gln Trp Asp Ser Asp Asn Ile Tyr Leu Ile Met Glu Phe Cys Ala Gly
                85                  90                  95

Gly Asp Leu Ser Arg Phe Ile His Thr Arg Arg Ile Leu Pro Glu Lys
                100                 105                 110

Val Ala Arg Val Phe Met Gln Gln Leu Ala Ser Ala Leu Gln Phe Leu
                115                 120                 125

His Glu Arg Asn Ile Ser His Leu Asp Leu Lys Pro Gln Asn Ile Leu
                130                 135                 140

Leu Ser Ser Leu Glu Lys Pro His Leu Lys Leu Ala Asp Phe Gly Phe
145                 150                 155                 160
```

Ala Gln His Met Ser Pro Trp Asp Glu Lys His Val Leu Arg Gly Ser
            165                 170                 175

Pro Leu Tyr Met Ala Pro Glu Met Val Cys Gln Arg Gln Tyr Asp Ala
            180                 185                 190

Arg Val Asp Leu Trp Ser Met Gly Val Ile Leu Tyr Asp Glu Thr Ser
            195                 200                 205

Phe Pro Cys Phe Ser Pro
    210

(2) INFORMATION FOR SEQ ID NO:7:

(i) SEQUENCE CHARACTERISTICS:
        (A) LENGTH: 1281 base pairs
        (B) TYPE: nucleic acid
        (C) STRANDEDNESS: single
        (D) TOPOLOGY: linear (vii) IMMEDIATE SOURCE:
        (A) LIBRARY: HMC1NOT01
        (B) CLONE: 2940

(xi) SEQUENCE DESCRIPTION: SEQ ID NO:7:

CGGCGTGGCA GATTCAGTTG TTTGCGGGCG GCCGGGAGAG TAGCAGTGCC TTGGACCCCA        60

GCTCTCCTCC CCCTTTCTCT CTAAGGATGG CCCAGAAGGA GAACTCCTAC CCCTGGCCCT       120

ACGGCCGACA GACGGCTCCA TCTGGCCTGA GCACCCTGCC CCAGCGAGTC CTCCGGAAAG       180

AGCCTGTCAC CCCATCTGCA CTTGTCCTCA TGAGCCGCTC CAATGTCCAG CCCACAGCTG       240

CCCCTGGCCA GAAGGTGATG GAGAATAGCA GTGGGACACC CGACATCTTA ACGCGGCACT       300

TCACAATTGA TGACTTTGAG ATTGGGCGTC CTCTGGGCAA AGGCAAGTTT GGAAACGTGT       360

ACTTGGCTCG GGAGAAGAAA AGCCATTTCA TCGTGGCGCT CAAGGTCCTC TTCAAGTCCC       420

AGATAGAGAA GGAGGGCGTG GAGCATCAGC TGCGCAGAGA GATCGAAATC CAGGCCCACC       480

TGCACCATCC CAACATCCTG CGTCTCTACA ACTATTTTTA TGACCGGAGG AGGATCTACT       540

TGATTCTAGA GTATGCCCCC CGCGGGGAGC TCTACAAGGA GCTGCAGAAG AGCTGCACAT       600

TTGACGAGCA GCGAACAGCC ACGGTCCGGG CGATCATGGA GGAGTTGGCA GATGCTCTAA       660

TGTACTGCCA TGGGAAGAAG GTGATTCACA GAGACATAAA GCCAGAAAAT CTGCTCTTAG       720

GGCTCAAGGG AGAGCTGAAG ATTGCTGACT TCGGCTGGTC TGTGCATGCG CCCTCCCTGA       780

GGAGGAAGAC AATGTGTGGC ACCCTGGACT ACCTGCCCCC AGAGATGATT GAGGGGCGCA       840

TGCACAATGA GAAGGTGGAT CTGTGGTGCA TTGGAGTGCT TTGCTATGAG CTGCTGGTGG       900

GGAACCCACC CTTTGAGAGT GCATCACACA ACGAGACCTA TCGCCGCATC GTCAAGGTGG       960

ACCTAAAGTT CCCCGCTTCC GTGCCCACGG GAGCCCAGGA CCTCATCTCC AAACTGCTCA      1020

GGCATAACCC CTCGGAACGG CTGCCCCTGG CCCAGGTCTC AGCCCACCCT TGGGTCCGGG      1080

CCAACTCTCG GAGGGTGCTG CCTCCCTCTG CCCTTCAATC TGTCGCCTGA TGGTCCCTGT      1140

CATTCACTCG GGTGCGTGTG TTTGTATGTC TGTGTATGTA TAGGGGAAAG AAGGGATCCC      1200

TAACTGTTCC CTTATCTGTT TTCTACCTCC TCCTTTGTTT AATAAAGGCT GAAGCTTTTT      1260

GTAAAAAAAA AAAAAAAAA A                                                1281

(2) INFORMATION FOR SEQ ID NO:8:

(i) SEQUENCE CHARACTERISTICS:
        (A) LENGTH: 2791 base pairs
        (B) TYPE: nucleic acid
        (C) STRANDEDNESS: single
        (D) TOPOLOGY: linear (vii) IMMEDIATE SOURCE:
    (A) LIBRARY: HEARNOT01
    (B) CLONE: 307624

(xi) SEQUENCE DESCRIPTION: SEQ ID NO:8:

| | | | | | |
|---|---|---|---|---|---|
| GGAGGCTGCA | GCCCAGCTCG | TCTCGGCGCC | CGCGTCGCCG | TCGCGAACCC | CCCGCCCCGC | 60 |
| TTCCGCCGCG | TCGGAATGAG | CTCCCGGAAA | GTGCTGGCCA | TTCAGGCCCG | AAAGCGGAGG | 120 |
| CCGAAAAGAG | AGAAACATCC | GAAAAAAAAT | CAAGCAGAAG | ATTGAGCTGC | TGATGTCAGT | 180 |
| TAACTCTGAG | AAGTCGTCCT | CTTCAGAAAG | GCCGGAGCCT | CAACAGAAAG | CTCCTTTAGT | 240 |
| TCCTCCTCCT | CCACCGCCAC | CACCACCACC | ACCGCCCCCT | TTGCCAGACC | CCACACCCCC | 300 |
| GGAGCCAGAG | GAGGAGATCC | TGGGATCAGA | TGATGAGGAG | CAAGAGGACC | CTGCGGACTA | 360 |
| CTGCAAAGGT | GGATATCATC | CAGTGAAAAT | TGGAGACCTC | TTCAATGGCC | GGTATCATGT | 420 |
| TATTAGAAAG | CTTGGATGGG | GGCACTTCTC | TACTGTCTGG | CTGTGCTGGG | ATATGCAGGG | 480 |
| GAAAAGATTT | GTTGCAATGA | AAGTTGTAAA | AAGTGCCCAG | CATTATACGG | AGACAGCCTT | 540 |
| GGATGAAATA | AAATTGCTCA | AATGTGTTCG | AGAAAGTGAT | CCCAGTGACC | CAAACAAAGA | 600 |
| CATGGTGGTC | CAGCTCATTG | ACGACTTCAA | GATTTCAGGC | ATGAATGGGA | TACATGTCTG | 660 |
| CATGGTCTTC | GAAGTACTTG | GCCACCATCT | CCTCAAGTGG | ATCATCAAAT | CCAACTATCA | 720 |
| AGGCCTCCCA | GTACGTTGTG | TGAAGAGTAT | CATTCGACAG | GTCCTTCAAG | GGTTAGATTA | 780 |
| CTTACACAGT | AAGTGCAAGA | TCATTCATAC | TGACATAAAG | CCGGAAAATA | TCTTGATGTG | 840 |
| TGTGGATGAT | GCATATGTGA | AAGAATGGCA | GCTGAGGCC | ACTGAGTGGC | AGAAAGCAGG | 900 |
| TGCTCCTCCT | CCTTCAGGGT | CTGCAGTGAG | TACGGCTCCA | CAGCAGAAAC | CTATAGGAAA | 960 |
| AATATCTAAA | AACAAAAAAA | AAAAACTGAA | AAAGAAACAG | AAGACGCAGG | CTGAGTTATT | 1020 |
| GGAGAAGCGC | CTGCAGGAGA | TAGAAGAATT | GGAGCGAGAA | GCTGAAAGGA | AATAATAGA | 1080 |
| AGAAAACATC | ACCTCAGCTG | CACCTTCCAA | TGACCAGGAT | GGCGAATACT | GCCCAGAGGT | 1140 |
| GAAACTAAAA | ACAACAGGAT | TAGAGGAGGC | GGCTGAGGCA | GAGACTGCAA | AGGACAATGG | 1200 |
| TGAAGCTGAG | GACCAGGAAG | AGAAAGAAGA | TGCTGAGAAA | GAAAACATTG | AAAAAGATGA | 1260 |
| AGATGATGTA | GATCAGGAAC | TTGCGAACAT | AGACCCTACG | TGGATAGAAT | CACCTAAAAC | 1320 |
| CAATGGCCAT | ATTGAGAATG | GCCCATTCTC | ACTGGAGCAG | CAACTGGACG | ATGAAGATGA | 1380 |
| TGATGAAGAA | GACTGCCCAA | ATCCTGAGGA | ATATAATCTT | GATGAGCCAA | ATGCAGAAAG | 1440 |
| TGATTACACA | TATAGCAGCT | CCTATGAACA | ATTCAATGGT | GAATTGCCAA | ATGGACGACA | 1500 |
| TAAAATTCCC | GAGTCACAGT | TCCCAGAGTT | TTCCACCTCG | TTGTTCTCTG | GATCCTTAGA | 1560 |
| ACCTGTGGCC | TGCGGCTCTG | TGCTTTCTGA | GGGATCACCA | CTTACTGAGC | AAGAGGAGAG | 1620 |
| CAGTCCATCC | CATGACAGAA | GCAGAACGGT | TTCAGCCTCC | AGTACTGGGG | ATTTGCCAAA | 1680 |
| AGCAAAAACC | CGGGCAGCTG | ACTTGTTGGT | GAATCCCCTG | GATCCGCGGA | ATGCAGATAA | 1740 |
| AATTAGAGTA | AAAATTGCTG | ACCTGGGAAA | TGCTTGTTGG | GTGCATAAAC | ACTTCACGGA | 1800 |
| AGACATCCAG | ACGCGTCAGT | ACCGCTCCAT | AGAGGTTTTA | ATAGGAGCGG | GGTACAGCAC | 1860 |
| CCCTGCGGAC | ATCTGGAGCA | CGGCGTGTAT | GGCATTTGAG | CTGGCAACGG | GAGATTATTT | 1920 |
| GTTTGAACCA | CATTCTGGGG | AAGACTATTC | CAGAGACGAA | GACCACATAG | CCCACATCAT | 1980 |
| AGAGCTGCTA | GGCAGTATTC | CAAGGCACTT | TGCTCTATCT | GGAAAATATT | CTCGGGAATT | 2040 |
| CTTCAATCGC | AGAGGAGAAC | TGCGACACAT | CACCAAGCTG | AAGCCCTGGA | GCCTCTTTGA | 2100 |
| TGTACTTGTG | GAAAAGTATG | GCTGGCCCCA | TGAAGATGCT | GCACAGTTTA | CAGATTTCCT | 2160 |
| GATCCCGATG | TTAGAAATGG | TTCCAGAAAA | ACGAGCCTCA | GCTGGCGAAT | GCCTTCGGCA | 2220 |

| | |
|---|---|
| TCCTTGGTTG AATTCTTAGC AAATTCTACC AATATTGCAT TCTGAGCTAG CAAATGTTCC | 2280 |
| CAGTACATTG GACCTAAACG GTGACTCTCA TTCTTTAACA GGATTACAAG TGAGCTGGCT | 2340 |
| TCATCCTCAG ACCTTTATTT TGCTTTGAGG TACTGTTGTT TGACATTTTG CTTTTTGTGC | 2400 |
| ACTGTGATCC TGGGGAAGGG TAGTCTTTTG TCTTCAGCTA AGTAGTTTAC TGACCATTTT | 2460 |
| CTTCTGGAAA CAATAACATG TCTCTAAGCA TTGTTTCTTG TGTTGTGTGA CATTCAAATG | 2520 |
| TCATTTTTTT GAATGAAAAA TACTTTCCCC TTTGTGTTTT GGCAGGTTTT GTAACTATTT | 2580 |
| ATGAAGAAAT ATTTTAGCTG AGTACATATAT AATTTACAAT CTTAAGAAAT TATCAAGTTG | 2640 |
| GAACCAAGAA ATAGCAAGGA AATGTACAAT TTTATCTTCT GGCAAAGGGA CATCATTCCT | 2700 |
| GTATTATAGT GTATGTAAAT GCACCCTGTA AATGTTACTT TCCATTAAAT ATGGGAGGGG | 2760 |
| GACTCAAATT TCAGAAAAGC TAAAAAAAAA A | 2791 |

(2) INFORMATION FOR SEQ ID NO:9:

(i) SEQUENCE CHARACTERISTICS:
        (A) LENGTH: 2446 base pairs
        (B) TYPE: nucleic acid
        (C) STRANDEDNESS: single
        (D) TOPOLOGY: linear (vii) IMMEDIATE SOURCE:
        (A) LIBRARY: NEUTFMT01
        (B) CLONE: 339963

(xi) SEQUENCE DESCRIPTION: SEQ ID NO:9:

| | |
|---|---|
| GCGACTCGGG GGATTCTAGG GCGACGGCGC TGCCGCCATT TTGTGGGGTG TTTGTCGCAG | 60 |
| CGGCCGAGGA GGGAAGACGG CAGTTTGGCG ACATTTCTCG GCCGAAGGGC CATTTGCTTT | 120 |
| TGCGGAGATG CGGCATTCCA AAAGAACTCA CTGTCCTGAT TGGGATAGCA GAGAAAGCTG | 180 |
| GGACATGAA AGCTATCGTG GAAGTCACAA GCGGAAGAGG AGATCTCATA GTAGCACACA | 240 |
| AGAGAACAGG CATTGTAAAC CACATCACCA GTTTAAAGAA TCTGATTGTC ATTATTTAGA | 300 |
| AGCAAGGTCC TTGAATGAGC GAGATTATCG GGACCGGAGA TACGTTGACG AATACAGGAA | 360 |
| TGACTACTGT GAAGGATATG TTCCTAGACA TTATCACAGA GACATTGAAA GCGGGTATCG | 420 |
| AATCCACTGC AGTAAATCTT CAGTCCGCAG CAGGAGAAGC AGTCCTAAAA GGAAGCGCAA | 480 |
| TAGACACTGT TCAAGTCATC AGTCACGTTC GATGAAATCC GTGGACACTT TGGGTGAAGG | 540 |
| AGCCTTTGGC AAAGTTGTAG AGTGCATTGA TCATGGCATG GATGGCATGC ATGTAGCAGT | 600 |
| GAAAATCGTA AAAAATGTAG GCCGTTACCG TGAAGCAGCT CGTTCAGAAA TCCAAGTATT | 660 |
| AGAGCACTTA AATAGTACTG ATCCCAATAG TGTCTTCCGA TGTGTCCAGA TGCTAGAATG | 720 |
| GTTTGATCAT CATGGTCATG TTTGTATTGT GTTTGAACTA CTGGGACTTA GTACTTACGA | 780 |
| TTTCATTAAA GAAACAGCT TTCTGCCATT TCAAATTGAC CACATCAGGC AGATGGCGTA | 840 |
| TCAGATCTGC CAGTCAATAA ATTTTTTACA TCATAATAAA TTAACCCATA CAGATCTGAA | 900 |
| GCCTGAAAAT ATTTTGTTTG TGAAGTCTGA CTATGTAGTC AAATATAATT CTAAAATGAA | 960 |
| ACGTGATGAA CGCACACTGA AAACACAGA TATCAAAGTT GTTGACTTTG GAAGTGCAAC | 1020 |
| GTATGATGAT GAACATCACA GTACTTGGT GTCTACCCGG CACTACAGAG CTCCCGAGGT | 1080 |
| CATTTTGGCT TTAGGTTGGT CTCAGCCTTG TGATGTTTGG AGCATAGGTT GCATTCTTAT | 1140 |
| TGAATATTAC CTTGGTTTCA CAGTCTTTCA GACTCATGAT AGTAAAGAGC ACCTGGCAAT | 1200 |
| GATGGAACGA ATATTAGGAC CCATACCACA ACACATGATT CAGAAAACAA GAAAACGCAA | 1260 |
| GTATTTTCAC CATAACCAGC TAGATTGGGA TGAACACAGT TCTGCTGGTA GATATGTTAG | 1320 |
| GAGACGCTGC AAACCGTTGA AGGAATTTAT GCTTTGTCAT GATGAAGAAC ATGAGAAACT | 1380 |

```
GTTTGACCTG GTTCGAAGAA TGTTAGAATA TGATCCAACT CAAAGAATTA CCTTGGATGA    1440

AGCATTGCAG CATCCTTTCT TTGACTTATT AAAAAAGAAA TGAAATGGGA ATCAGTGGTC    1500

TTACTATATA CTTCTCTAGA AGAGATTACT TAAGACTGTG TCAGTCAACT AAACATTCTA    1560

ATATTTTTGT AAACATTAAA TTATTTTGTA CAGTTAAGTG TAAATATTGT ATGTTTTGTA    1620

TCAATAGCAT AATTAACTTG TTAAGCAAGT ATGGTCTTGA TAATGCATTA GAAAAATTAA    1680

AATTAATTTT TCTTTTTGAA ATTACCATTT TTAAATACCT TTGAAATATC CTTTGTGTCC    1740

AGTGATAAAT GTGATTGATC TTGCCTTTTG TACATGGAGG TCACCTCTGA AGTGATTTTT    1800

TTTGAGTAAA AGGAAATCTT GACTACTTTA TATTCTTAAA GGAATATTCT TTATATACTT    1860

CAAATTTAGA ACTTAACTTT AAAAGTTTTT CTTCTGTAAT TGTTGAACGG GTGATTATTA    1920

TTAACTCTAG ATAAGCAGGT ACTAGAAACC AAAACTCAGA AAATGTTTAC TGTTAGAATT    1980

CTATTAAATT TTAAGTGTTG TATTCTTTTT CATTGGGTGA TGTCAGGGTG ATAACCAGAC    2040

ATTCATGGAA AGGCATGCAG TTTGTCCATT GTGACAGTTT GTTTAATAAA ACCACATACA    2100

CACTTTATTT AAGATTAAAA TCTAACTGGA AAGTCAGCTT GGAAAATGGA CATTTCCAAG    2160

TATGTTTGGT GAGTCACAGA TATAAAAATA GAAATTCTGA TGAGAGGTTT CAGTTTTTAA    2220

TACCAAGTCC TTAGGAGTCT TAACATTGGC CAGCATCTGT TTATCAAATG ACATAAATAC    2280

GTAAACCTAT AAGAATTAAG TTTATTAATT AGGCAATTTA TGTCTGTGAT AATTCTTACG    2340

GGAGAAAGAG GATTTGATTG GAAAGCAGTT TGGGAAGAAA GTGCTGCTGA AATTTCCAGA    2400

ATTTAATTGA TTGGTTACAT AAACTTTTTG ACTTCAAAAA AAAAAA                   2446

(2) INFORMATION FOR SEQ ID NO:10:

(i) SEQUENCE CHARACTERISTICS:
            (A) LENGTH: 1929 base pairs
            (B) TYPE: nucleic acid
            (C) STRANDEDNESS: single
            (D) TOPOLOGY: linear (vii) IMMEDIATE SOURCE:
             (A) LIBRARY: MMLR1DT01
             (B) CLONE: 472480

(xi) SEQUENCE DESCRIPTION: SEQ ID NO:10:

GGGGCGGGCG CAGGATGAGG GCGGCCATTG CTGGGGCTCC GCTTCGGGGA GGAGGACGCT      60

GAGGAGGCGC CGAGCCGCGC AGGCTGGCGG GGGAGGCGCC CGCACCGACG CGGGGCCCAT     120

GGCCAGGACC ACCAGCCAGC TGTATGACGC CGTGCCCATC CAGTCCAGCG TGGTGTTATG     180

TTCCTGCCCA TCCCCATCAA TGGTGAGGAC CCAGACTGAG TCCAGCACGC CCCTGGCAT      240

TCCTGGTGGC AGCAGGCAGG GCCCCGCCAT GGACGGCACT GCAGCCGAGC CTCGGCCCGG     300

CGCCGGCTCC CTGCAGCATG CCCAGCCTCC GCCGCAGCCT CGGAAGAAGC GGCCTGAGGA     360

CTTCAAGTTT GGGAAAATCC TTGGGGAAGG CTCTTTTTCC ACGGTTGTCC TGGCTCGAGA     420

ACTGGCAACC TCCAGAGAAT ATGCGATTAA AATTCTGGAG AAGCGACATA TCATAAAAGA     480

GAACAAGGTC CCCTATGTAA CCAGAGAGCG GGATGTCATG TCGCGCCTGG ATCACCCCTT     540

CTTTGTTAAG CTTTACTTCA CATTTCAGGA CGACGAGAAG CTGTATTTCG GCCTTAGTTA     600

TGCCAAAAAT GGAGAACTAC TTAAATATAT TCGCAAAATC GGTTCATTCG ATGAGACCTG     660

TACCCGATTT TACACGGCTG AGATTGTGTC TGCTTTAGAG TACTTGCACG GCAAGGGCAT     720

CATTCACAGG GACCTTAAAC CGGAAAACAT TTTGTTAAAT GAAGATATGC ACATCCAGAT     780

CACAGATTTT GGAACAGCAA AAGTCTTATC CCCAGAGAGC AAACAAGCCA GGGCCAACTC     840
```

```
ATTCGTGGGA ACAGCGCAGT ACGTTTCTCC AGAGCTGCTC ACGGAGAAGT CCGCCTGTAA      900

GAGTTCAGAC CTTTGGGCTC TTGGATGCAT AATATACCAG CTTGTGGCAG GACTCCCACC      960

ATTCCGAGCT GGAAACGAGT ATCTTATATT TCAGAAGATC ATTAAGTTGG AATATGACTT     1020

TCCAGAAAAA TTCTTCCCTA AGGCAAGAGA CCTCGTGGAG AAACTTTTGG TTTTAGATGC     1080

CACAAAGCGG TTAGGCTGTG AGGAAATGGA AGGATACGGA CCTCTTAAAG CACACCCGTT     1140

CTTCGAGTCC GTCACGTGGG AGAACCTGCA CCAGCAGACG CCTCCGAAGC TCACCGCTTA     1200

CCTGCCGGCT ATGTCGGAAG ACGACGAGGA CTGCTATGGC AATTATGACA ATCTCCTGAG     1260

CCAGTTTGGC TGCATGCAGG TGTCTTCGTC CTCCTCCTCA CACTCCCTGT CAGCCTCCGA     1320

CACGGGCCTG CCCCAGAGGT CAGGCAGCAA CATAGAGCAG TACATTCACG ATCTGGACTC     1380

GAACTCCTTT GAACTGGACT ACAGTTTTC CGAAGATGAG AAGAGGTTGT TGTTGGAGAA      1440

GCAGGCTGGC GGAAACCCTT GGCACCAGTT TGTAGAAAAT AATTTAATAC TAAAGATGGG     1500

CCCAGTGGAT AAGCGGAAGG GTTTATTTGC AAGACGACGA CAGCTGTTGC TCACAGAAGG     1560

ACCACATTTA TATTATGTGG ATCCTGTCAA CAAAGTTCTG AAAGGTGAAA TTCCTTGGTC     1620

ACAAGAACTT CGACCAGAGG CCAAGAATTT TAAAACTTTC TTTGTCCACA CGCCTAACAG     1680

GACGTATTAT CTGATGGACC CCAGCGGGAA CGCACACAAG TGGTGCAGGA AGATCCAGGA     1740

GGTTTGGAGG CAGCGATACC AGAGCCACCC GGACGCCGCT GTGCAGTGAC AGTGTGCGGC     1800

CGGGCTGCCC TTCGCTGCCA GGACACCTGC CCCAGCGCGG CTTGGCCGCC ATCCGGGACG     1860

CTTCCAGACC ACCTGCCAGC CATCACAATG GGGACGCATG ACGGCGGAAA CCTTGCANGA     1920

TTTTTATTT                                                           1929

(2) INFORMATION FOR SEQ ID NO:11:

(i) SEQUENCE CHARACTERISTICS:
        (A) LENGTH: 2393 base pairs
        (B) TYPE: nucleic acid
        (C) STRANDEDNESS: single
        (D) TOPOLOGY: linear (vii) IMMEDIATE SOURCE:
        (A) LIBRARY: COLNTUT02
        (B) CLONE: 1222984

(xi) SEQUENCE DESCRIPTION: SEQ ID NO:11:

GATACTCGTT TGTAGTTTCA TAAACATTGA TGTTGGGTCA ATCATGTTCT CAATGTATTT       60

AACCATGTGT TTTTAAATTN TTTAATTTAG CCCGGCAGAG CGCGTTATCA AATTGAGAAT      120

CTGATGGTAT GGCATTAATC ACCTTGAGGA AGAACCTTTA TCGTTTATCT GATTTTCAGA      180

TGCATAGAGC TCTGGCTGCT TTAAAAAATA AACCTCTAAA TCATGTTCAC AAGGTAGTCA      240

AGGAGCGTCT GTGCCCTTGG TTGTGTTCAC GACAACCTGA GCCTTTCGGG GTCAGATTCC      300

ATCATGCCCA TTGTAAAAAG TTTCATTCGA AAAATGAAA TGACCTTCAT CCACTCGGTG      360

GACCAGTGTT CTCTCAAGTA TCTGACTGCG ACAGGCTTGA ACAAAATGTT AAAAATGAGG      420

AGAGTCAGAT GTTTTACAGG AGACTGAGCA ACTTGACTTC ATCAGAAGAA GTGCTAAGTT      480

TTATAAGCAC GATGGAAACC CTGCCTGACA CTATGGCAGC AGGAGCTTTA CAACGGATTT      540

GTGAAGTGGA AAAAAGGAT GGTGATCAAG GGCTGCCAAA AGGAATACTG GAGAAATAGCA      600

TCTTTCAAGC TTTATGCTTT CAGTTTGAAA AGGAGCCCTC ACAGCTGTCA AACACTAGTT      660

TAGTGACTGC TTTGCAAGCT CTGATTCTGT TGCATGTGGA TCCTCAAAGT AGCCTGTTGC      720

TGAACCTGGT GGCAGAATGC CAAAATCGTC TCAGAAAAGG TGGCATGGAA GTTCGCAATC      780

TTTGTATTCT TGGGGAAAGT CTGATTACAC TGCACAGTTC AGGTTGTGTG ACACTAGAAC      840
```

```
TCATTATAAA TCAACTTCAA GGTGAAAAAT TGGAAACATT TACCCCGGAG GATATTGTGG      900

CCCTTTATAG AATCTTGCAG GCATGTACTG AAAAAGTGGA TGAACACCAA ACATTTTTAA      960

ATAAGATAAA CAACTTTTCC CTATCAATAG TTTCCAACCT GAGTCCTAAA TTGATTAGCC     1020

AAATGCTCAC TGCCCTGGTG GTTCTTGATC AAAGTCAAGC ATTTCCTCTG ATTATAAAAT     1080

TGGGCAAATA TGTCGTGAGG CATGTCCCAC ATTTCACTAA CGAGGAGCTT AGGAGAGTCT     1140

TGGAGGCGTT CATATATTTT GGGCACCATG ACACATTTTT TACAAAGCC CTAGAGCATC      1200

GTGTAGCTGC GGTGTGCCTC ACGTTGGATC CTGAAGTTGT CTGCAGGGTC ATGGAGTACT     1260

GCAGTAGAGA ACTGATTCTT TCAAAACCCA TCCTCAATGC AGTGGCAGAA ACTTTTGTTT     1320

GCCAAACAGA AAAATTTTCA CCTCGTCAGA TTTCTGCCTT AATGGAACCA TTTGGGAAAC     1380

TCAATTATTT GCCACCAAAT GCCTCTGCTT TATTTAGAAA GCTGGAAAAC GTGCTATTCA     1440

CTCATTTCAA TTATTTTCCA CCCAAATCAT TATTGAAACT TCTTCATTCA TGTTCACTTA     1500

ATGAATGCCA TCCAGTCAAC TTTCTGGCAA AAATATTCAA GCCTCTTTTC CTTCAACGGC     1560

TGCAAGGTAA AGAATCTCAT TTGGACACAT TGAGTCGGGC ACAACTGACC CAACTTTTCT     1620

TAGCCTCAGT CCTGGAATGC CCTTTCTATA AGGGTCCAAA ACTCCTTCCT AAATATCAAG     1680

TGAAGTCATT TCTTACCCCA TGCTGTTCCC TGGAGACCCC TGTGGATTCT CAGCTTTATA     1740

GATATGTGAA GATTGGGCTG ACTAACCTTT TAGGAGCAAG ATTATATTTT GCTCCAAAAG     1800

TGTTGACACC CTATTGTTAT ACAATAGATG TTGAAATTAA ATTAGATGAA GAAGGATTTG     1860

TATTGCCATC CACAGCTAAT GAAGATATCC ATAAAAGGAT AGCACTGTGT ATTGATGGTC     1920

CAAAAAGGTT TTGCTCCAAT AGCAAACACT TACTGGGGAA AGAAGCTATT AAACAAAGAC     1980

ACCTACAGTT ACTCGGTTAT CAAGTTGTTC AGATCCCCTA TCATGAGATT GGGATGCTAA     2040

AATCAAGACG TGAATTGGTG GAATATTTAC AAAGAAAACT GTTTTCTCAA AACACTGTTC     2100

ATTGGTTGCA AGAATGAATA CTGACTTCAG AACTCAAACA ATGGAAGAAC TTGCATTTTT     2160

ATGGAACTCA GTATTAAAAG AAAAATATAA TGTGAATTAG CCACTTTGCA GAATATGTTC     2220

TAGACTGGTG ATCTGAAAGC ATCTGTAGTT TTCCTTATAC TATGTATACA TTTATTGTGG     2280

TAAAATTTAA AATTAATTTT AATTTAATAC TAGTGTCATA GATACTTTTT GTACATCAAA     2340

CAATTGATCA TGTGCTGTAA AGGAATTCAA TGAATAAATG TTATTTTTAA GTA           2393
```

(2) INFORMATION FOR SEQ ID NO:12:

(i) SEQUENCE CHARACTERISTICS:
        (A) LENGTH: 2746 base pairs
        (B) TYPE: nucleic acid
        (C) STRANDEDNESS: single
        (D) TOPOLOGY: linear (vii) IMMEDIATE SOURCE:
        (A) LIBRARY: OVARNOT03
        (B) CLONE: 2061844

(xi) SEQUENCE DESCRIPTION: SEQ ID NO:12:

```
GCCCGCGCGG GCGCAGGCGG CCGGGATGGC GGGGCCCGGC TGGGGTCCCC CGCGCCTGGA       60

CGGCTTCATC CTCACCGAGC GCCTGGGCAG CGGCACGTAC GCCACGGTGT ACAAGGCCTA      120

CGCCAAGAAG GACACTCGTG AAGTGGTAGC CATAAAGTGT GTAGCCAAGA AAGTCTGAA       180

CAAGGCATCG GTGGAGAACC TCCTCACGGA GATTGAGATC CTCAAGGGCA TTCGACATCC      240

CCACATTGTG CAGCTGAAAG ACTTTCAGTG GGACAGTGAC AATATCTACC TCATCATGGA      300

GTTTTGCGCA GGGGGCGACC TGTCTCGCTT CATCCATACC CGCAGGATTC TGCCTGAGAA      360
```

```
GGTGGCGCGT GTCTTCATGC AGCAATTAGC TAGCGCCCTG CAATTCCTGC ATGAACGGAA    420

TATCTCTCAC CTGGATCTGA AGCCACAGAA CATTCTACTG AGCTCCTTGG AGAAGCCCCA    480

CCTAAAACTG GCAGACTTTG GTTTCGCACA ACACATGTCC CCGTGGGATG AGAAGCACGT    540

GCTCCGTGGC TCCCCCCTCT ACATGGCCCC CGAGATGGTG TGCCAGCGGC AGTATGACGC    600

CCGCGTGGAC CTCTGGTCCA TGGGGGTCAT CCTGTATGAT GAGACCTCTT TTCCCTGCTT    660

CTCACCCTGA GGCTACAGT TTCCTCAGGC AAGGCCTCTC TGGGCCACTT CTGAAGGGTT     720

CTGATGAAAA CTGACTGCTG GCCCAGGGCC CCTGCTGAGG GGCGTCAGGC CAGGCTTGAC    780

CCATTCCCTC CCAGCCTCCG CTCTGCCTCC CTTCCACAGA AGCCCTCTTC GGGCAGCCCC    840

CCTTTGACCT CCAGGTCGTT CTCGGAGCTG AAGAGAAGA TCCGTAGCAA CCGGGTCATC     900

GAGCTCCCCT TGCGGCCCCT GCTCTCCCGA GACTGCCGGG ACCTACTGCA GCGGCTCCTG    960

GAGCGGGACC CCAGCCGTCG CATCTCCTTC CAGGACTTCT TTGCGCACCC CTGGGTGGAC   1020

CTGGAGCACA TGCCCAGTGG GGAGAGTCTG GGGCGAGCAA CCGCCCTGGT GGTGCAGGCT   1080

GTGAAGAAAG ACCAGGAGGG GGATTCAGCA GCCGCCTTAT CACTCTACTG CAAGGCTCTG   1140

GACTTCTTTG TACCTGCCCT GCACTATGAA GTGGATGCCC AGCGGAAGGA GGCAATTAAG   1200

GCAAAGGTGG GGCAGTACGT GTCCCGGGCT GAGGAGCTCA AGGCCATCGT CTCCTCTTCC   1260

AATCAGGCCC TGCTGAGGCA GGGGACCTCT GCCCGAGACC TGCTCAGAGA GATGGCCCGG   1320

GACAAGCCAC GCCTCCTAGC TGCCCTGGAA GTGGCTTCAG CTGCCATGGC CAAGGAGGAG   1380

GCCGCCGGCG GGGAGCAGGA TGCCCTGGAC CTGTACCAGC ACAGCCTGGG GGAGCTACTG   1440

CTGTTGCTGG CAGCGGAGCC CCCGGGCCGG AGGCGGGAGC TGCTTCACAC TGAGGTTCAG   1500

AACCTCATGG CCCGAGCTGA ATACTTGAAG GAGCAGGTCA AGATGAGGGA ATCTCGCTGG   1560

GAAGCTGACA CCCTGGACAA AGAGGGACTG TCGGAATCTG TTCGTAGCTC TTGCACCCTT   1620

CAGTGACCCT AGAAGAATGA TTGGACAGAT GTGAGCCATC TGGAGCAGAG GGGCACTAAC   1680

CCAGGCTGAC GCCAAGAATG AAGTGGCCCA CTGCAGCCCT GGCGAGCAGG CTTCTTGGAT   1740

GGACAGTGCT GAGACCCCCA TATCCCAGAG TCCCCAGCCT CCCTCAGGTT ACTCTGCACC   1800

CCACAGATGG TTTGATGGCT GTGCTGTATA CTGGAGGGGA GGGCAGGACT CTGGGAGAAC   1860

AGCACTTCTT TCATGAGACC TTTGTTACTC GGTGGTTACT GGGTCCTGTG CCTGTCCGTT   1920

TTGGGGCATG CAGCCCTCTA TCATTTTTGG CTCCGAGAAG AGGGCAAGGG GCCCCGCAG    1980

GGCACTTCTG TGCTTGCCCT CGCCCTGCCA GCAGGCAGCT GTGCCCCTGG CCTGCCCTTC   2040

CCGGGACCCC TTATTCCAAC TCAGCTCCTC TTTGCACTGG AATGGGCAC TCCAACACCC    2100

CTCAGGGACC ACCCTCCCCA CAGTATGCAC TCAGCCCCAC AGAACCCACC AGTCTTTCTG   2160

GGAACTCACA CCTGCCCGCC ATCTTGGTAC TTTAGGTTAA TCCCTCAAGC ATGAAAGCTG   2220

GATCTTTTGG GGTTTAAGAA GCCCAAGCCT TGTTCCTGCC CTGGCCTAGG GAGCACTCAG   2280

GAGGGTTCCT TGGTCCTCAT CTCTCCCACC TCCGTTCCCT CTGGGCCCCA CACTAGCCAC   2340

AGCGCGGGCC TTGTGCTGGA GTTTGAGCCT GGGACAGGGA GAGGGAGGCT TGGAGACAGT   2400

CTGACCCAGT GCCCTCTAGG CCACCCACTT CTAGGCCTGC CCTGCCGCCG TGGAGCCCTG   2460

GGCAAGCTCT TTCCCCTTTC TGGGCCTGGG TCTCCCCATC TCTTCAATGG GGCTGATACC   2520

TTCACAGCCC ACAGCATGGG CACTTATGAG GACAAAGTGA ATTTAACCTG GAAAAGAATG   2580

TATTTGAGAG TTTCTTTTAA ATAATCAGCG GGTGTTGGTG ATTTGTAGCC CTTCTGCCCT   2640

TAAATGCTTC CTTGGGCAAG AGCTGTCTGT CCTCCCTGCA GGAGGCTGAG TGTGAAGAGT   2700

ATCATTCATT GTTTCTCTAT TAAATTATTT TCTCTAAAAA AAAAAA                  2746
```